US006919340B2

United States Patent
Currie et al.

(10) Patent No.: US 6,919,340 B2
(45) Date of Patent: Jul. 19, 2005

(54) IMIDAZO[1,2-A]PYRAZIN-8-YLAMINES, METHOD OF MAKING, AND METHOD OF USE THEREOF

(75) Inventors: Kevin S. Currie, North Branford, CT (US); Robert W. DeSimone, Durham, CT (US); Douglas A. Pippin, Branford, CT (US); James W. Darrow, Wallingford, CT (US); Scott A. Mitchell, East Haven, CT (US)

(73) Assignee: Cellular Genomics, Inc., Branford, CT (US)

( * ) Notice: Subject to any disclaimer, the term of this patent is extended or adjusted under 35 U.S.C. 154(b) by 121 days.

(21) Appl. No.: 10/419,682

(22) Filed: Apr. 21, 2003

(65) Prior Publication Data

US 2003/0212073 A1 Nov. 13, 2003

Related U.S. Application Data

(60) Provisional application No. 60/374,213, filed on Apr. 19, 2002.

(51) Int. Cl.[7] .................. A01N 43/58; A01N 43/60; A61K 31/495; A61K 31/50; C07D 471/00

(52) U.S. Cl. ........................ 514/249; 544/350

(58) Field of Search .................. 514/249; 544/350

(56) References Cited

U.S. PATENT DOCUMENTS

| 5,593,997 | A | 1/1997 | Dow et al. .................. 514/258 |
| 5,658,857 | A | 8/1997 | Andree et al. ............... 504/228 |
| 5,783,576 | A | 7/1998 | Roos et al. .................. 514/242 |
| 2004/0063715 | A1 | 4/2004 | Paruch et al. |
| 2004/0067951 | A1 | 4/2004 | DeSimone et al. |
| 2004/0072835 | A1 | 4/2004 | Paruch et al. |
| 2004/0220189 | A1 | 11/2004 | Sun et al. |

FOREIGN PATENT DOCUMENTS

| DE | 0 43 37 609 A1 | 5/1995 |
| EP | 0 480 713 A1 | 10/1991 |
| WO | WO 88/04298 | 6/1988 |
| WO | WO 95/12594 | 5/1995 |
| WO | WO 96/04298 | 2/1996 |
| WO | WO 96/34866 | 11/1996 |
| WO | WO 99/28322 | 6/1999 |
| WO | WO 01/27119 A2 | 4/2001 |

(Continued)

OTHER PUBLICATIONS

Banerjee et al, "Experimental Models of Colorectal Cancer" Diseases of the Colon and Rectum, vol. 41(4), pp. 490–505.*

(Continued)

*Primary Examiner*—James O. Wilson
*Assistant Examiner*—Zachary C. Tucker
(74) *Attorney, Agent, or Firm*—Finnegan, Hedneson, Farabow, Garrett & Dunner

(57) ABSTRACT

A novel composition comprises a compound of Formula 1

(1)

the pharmaceutically acceptable salts, hydrates, solvates, crystal forms, diastereomers, prodrugs, or mixtures thereof. The composition is of particular utility in the treatment of kinase-implicated disorders.

34 Claims, 2 Drawing Sheets

FOREIGN PATENT DOCUMENTS

| WO | WO 02/10170 A1 | 2/2002 |
|---|---|---|
| WO | WO 02/30428 A1 | 4/2002 |
| WO | WO 02/060492 A1 | 8/2002 |
| WO | WO 02/076985 | 10/2002 |
| WO | WO 2003/089434 | 10/2003 |
| WO | WO 2004/022562 | 3/2004 |
| WO | WO 2004/026310 | 4/2004 |
| WO | WO 2004/026877 | 4/2004 |
| WO | WO 2004/072080 | 8/2004 |
| WO | WO 2004/072081 | 8/2004 |

OTHER PUBLICATIONS

Ulrich et al, "Pancreatic Cell Lines: A Review" Pancreas, vol. 24(2), pp. 111–120 (2002).*

International Search Report Dated Oct. 22, 2003.

Vitse, et al. "New Imidazo [1,2-a]pyrazine Derivatives with Bronchodilatory and Cyclic Nucleotide Phosphodiesterase Inhibitory Activities". Bioorganic & Medicinal Chemistry 7 (1999) 1059–1065.

Hanks, Steven K. Protein Kinase Classification. 1994. pp. 1–4. http://pkr.sdsc.edu/html/pk_classification/pk_catalytic/pk_hanks_class.html.

Jeffrey, Trina K. et al. "Phosphodiesterase III and V Inhibitors on Pulmonary Artery from Pulmonary Hypertensive Rats: Differences Between Early and Established Pulmonary Hypertension." Journal of Cardiovascular Pharmacology. 1998. vol. 32, pp. 213–219.

Lumma, William C. et al. "Piperazinylimidazo[1,2-a]pyrazines with Selective Affinity for in Vitro a–Adrenergic Receptor Subtypes." J. Med. Chem. 1983. vol. 26, pp. 357–363.

"Protein Kinases in Disease." http://bioinformatics.weizmann.ac.il/Kinases/pkr/pk_medicine.html.

Stenburg, Kaj A.E. et al. "KinMutBase, a database of human disease–causing protein kinase mutations." Nucleic Acids Research. 2000. vol. 28, pp. 369–371.

International Search Report and Written Opinion dated Dec. 8, 2004, for Application No. PCT/US2004/021150, International filing date Jun. 30, 2004.

International Search Report and Written Opinion dated Dec. 30, 2004, for Application No. PCT/US2004/018227, International filing date Jun. 4, 2004.

Ding et al. (2002) "A Combinatorial Scaffold Approach toward Kinase–Directed Heterocycle Libraries," JACS, 124(8): 1594–1596.

Written Opinion dated Dec. 5, 2003, for Application No. PCT/US03/12222, International filing date Apr. 21, 2003.

Second Written Opinion dated Apr. 13, 2004, for Application No. PCT/US03/12222, International filing date Apr. 21, 2003.

International Preliminary Examination Report dated Aug. 3, 2004, for Application No. PCT/US03/12222, International filing date Apr. 21, 2003.

International Search Report dated Feb. 9, 2004, for Application No. PCT/US03/28329, International filing date Sep. 9, 2003.

Written Opinion dated Jul. 6, 2004, for Application No. PCT/US03/28329, International filing date Sep. 9, 2003.

International Preliminary Examination Report dated Oct. 27, 2004, for Application No. PCT/US03/28329, International filing date Sep. 9, 2003.

International Search Report and Written Opinion dated Jul. 7, 2004, for Application No. PCT/US2004/003922, International filing date Feb. 10, 2004.

* cited by examiner

IMIDAZO[1,2-A]PYRAZIN-8-YLAMINES, METHOD OF MAKING, AND METHOD OF USE THEREOF

CROSS REFERENCE TO RELATED APPLICATIONS

This application claims the benefits of U.S. Provisional Patent Application Ser. No. 60/374,213 filed Apr. 19, 2002, which is fully incorporated herein by reference.

BACKGROUND

This invention relates to certain imidazo[1,2-a]pyrazin-8-ylamines and related compounds, which when appropriately substituted are modulators of kinase activity. This invention also relates to pharmaceutical compositions comprising such compounds, and to the use of such compounds in treating a variety of kinase-associated disorders. Additionally, this invention relates to the use of such compounds as probes for the identification of kinases of therapeutic interest.

One of the central post-translational control elements in eukaryotic signal transduction is the phosphorylation of the hydroxyl moiety of serine, threonine, or tyrosine. The phosphorylation state of a given protein can govern its enzyme activity, stability, protein-protein binding interactions, and cellular distribution. Phosphorylation and dephosphorylation is thus a "chemical switch" that allows the cell to transmit signals from the plasma membrane to the nucleus, and to ultimately control gene expression. Although the exact mechanisms of signal transduction have yet to be elucidated, kinases are involved in the control of cell metabolism, growth, differentiation, and apoptosis. These signaling mechanisms affect the onset of cancer, metabolic disorders (for example diabetes), inflammation, immune system disorders, and neurodegeneration. Certain kinases have been implicated in cell proliferation and carcinogenesis. For example, many human cancers are caused by disregulation of a normal protein (e.g., when a proto-oncogene is converted to an oncogene through a gene translocation). Because kinases are key regulators they are ideal drug design targets.

Inhibitors of kinases are among the most important pharmaceutical compounds known. Tyrosine kinase inhibitors are useful in inhibiting T-cell proliferation, and thus they are useful as immunosuppressive agents for the prevention or treatment of graft rejection following transplant surgery and for the prevention or treatment of autoimmune diseases such as rheumatoid arthritis and psoriasis. Other tyrosine kinase inhibitors have been described, for example, in U.S. Pat. No. 5,593,997 to Dow et al. Erlotinib (CP-358774) teach a quinazoline derivative under development as an orally active epidermal growth factor receptor (EGFR) tyrosine kinase inhibitor for treatment of solid tumors including non-small cell lung cancer (NSCLC), pancreatic cancer, breast cancer, and neck cancer. Gleevec and Imatinib (STI-571), from Novartis, are tyrosine kinase inhibitors indicated for treatment of chronic myelogenous leukemia (CML), prostate tumors, and gastrointestinal stromal tumors, among others. AstraZeneca is developing gefitinib (ZD-1839; Iressa), an inhibitor of epidermal growth factor receptor 1 (EGFR1) tyrosine kinase, for the potential treatment of cancers which over-express EGF receptors, including non-small cell lung cancer (NSCLC) and other solid tumors such as breast tumors. CEP-1347 (Cephalon Inc.) is an indolcarbazole choline acetyltransferase inhibitor and c-jun N-terminal kinase inhibitor for treatment of Alzheimer's disease, Parkinson's disease, and AIDS-related peripheral neuropathy. Cephalon is also developing CEP-701, an orally active tyrosine kinase inhibitor for the potential treatment of prostate and other cancers. A PDGF receptor tyrosine kinase inhibitor (SU-101, leflunomide) is being investigated for treatment of various cancers and rheumatoid arthritis. Sugen has also investigated the anti-cancer effects of the FLK-1 tyrosine kinase inhibitor Semaxanib, particularly for colorectal and lung cancers, leukemia, Kaposi's sarcoma, and others.

Serine/threonine kinase inhibitors are also pharmaceutically important. Eli Lilly is developing LY333531 (ruboxistaurin), an inhibitor of protein kinase C beta, for treatment of diabetic macular edema and diabetic retinopathy. Flavopirodol (Aventis) is a synthetic flavonoid inhibitor of cyclin-dependent kinases, is under development for treatment of mantle cell lymphoma (MCL) and fludar refractory chronic lymphocytic leukemia (CLL). One Raf kinase inhibitor (BAY-43-9006, Bayer) is in development for treatment of solid tumors and myeloid leukemia, and another (ISIS 5132, Isis) is being investigated for treatment of ovarian cancer. Several p38 mitogen-activated protein kinase inhibitors (VX-745, VX-702, and VX-850, Vertex, and SCIO-469, Scios) have been investigated for treatment of inflammation, rheumatoid arthritis, and myelodysplastic syndrome (MDS).

Highly selective, cell-permeable modulators of one or more individual kinases would thus be useful in the treatment of various kinase-implicated disorders. Such compounds would also be useful for the systematic investigation of the cellular function of one or more kinases, and thus, would provide invaluable tools for the identification of various kinases of therapeutic interest.

The compounds most closely related structurally to those described herein are a series of imidazolopyrazines described in WO 02/060492, as JAK inhibitors for the treatment of immune disorders. A series of piperazinylimidazo[1,2a]pyrazines are described by Lumma *J. Med. Chem.* 1983, 26, 357–363 as displaying affinity for α-adrenergic receptors. Other imidazo[1,2-a]pyrazines have been reported to be useful as bronchodilators and phosphodiesterase inhibitors (see, for example, *Bioorg. Med Chem.* 1999, pages 1059–1065). Effects on pulmonary hypertension have also been reported (see, for example, *J. Cardiovase. Pharmacol.* 1998, volume 32, no. 2, pages 213–219). The compounds described in these publications are not within the scope of the present invention.

SUMMARY

In one embodiment, this invention is directed to a composition comprising a compound of Formula 1:

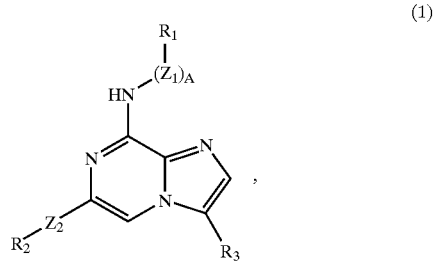

(1)

the pharmaceutically acceptable salts, hydrates, solvates, crystal forms, diastereomers, prodrugs, or mixtures thereof, wherein $R_1$ is hydrogen; cyclo-($C_3$–$C_6$ alkyl)-methyl; straight or branched chain $C_1$–$C_7$ alkyl, in which the branched alkyl chains may form a 3 to 7 member heteroalkyl or alkyl ring; sulfonamide; $C_1-C_6$ alkoxy; $(C_1-C_6)$-alkyl-oxy-$(C_1-C_6)$alkoxy; mono- or di($C_1-C_6$ alkyl)amino; mono- or di($C_1-C_6$ alkyl)amino($C_1-C_6$ alkyl); or phenyl or heteroaryl ring which may be unsubstituted, or mono-, di- or trisubstituted with one or more of hydroxy, nitro, cyano, amino, sulfonamide, halogen, $C_1-C_6$ alkyl, $C_1-C_6$ perfluoroalkyl, $C_1-C_6$ perfluoroalkoxy, $C_1-C_6$ perfluoroalkyl, $C_1-C_6$ perfluoroalkoxy, $C_1-C_6$ alkoxy, mono- or di($C_1-C_6$ alkyl)amino, or mono- or di($C_1-C_6$ alkyl)amino($C_1-C_6$ alkyl); and, $R_2$ is straight or branched chain $C_1-C_7$ alkyl, in which the branched alkyl chains may form a 3–7 member heteroalkyl or alkyl ring; cyclo-($C_3-C_6$ alkyl)-methyl; $C_1-C_6$ alkoxy, except when $Z_2$ is phenylene and A is 0 and $R_1$ is straight or branched chain $C_1-C_7$ alkyl (but not cycloalkyl), phenyl, or phenyl substituted with hydroxy, nitro, cyano, amino, $C_1-C_6$ alkoxy, or halogen, or when $Z_2$ is phenylene and A is 1, $Z_1$ is —$C(R_4)(R_5)$— wherein m is 1, 2, or 3 and $R_1$ is straight or branched chain $C_1-C_7$ alkyl (but not cycloalkyl), phenyl, or phenyl substituted with hydroxy, nitro, cyano, amino, $C_1-C_6$ alkoxy, or halogen, or when $Z_2$ is —$C(R_7)(R_8)$— wherein n is 1, 2, or 3, each occurrence of $R_7$ and $R_8$ is independently straight or branched chain $C_1-C_6$ alkyl or halogen and $R_2$ is $C_1-C_6$ alkoxy or phenyl substituted with nitro; $(C_1-C_6)$-alkyl-oxy-$(C_1-C_6)$alkoxy; or phenyl or heteroaryl which may be unsubstituted, mono-, di- or trisubstituted with one or more of hydroxy, nitro (except when $Z_2$ is phenylene and A is 0 and $R_1$ is straight or branched chain $C_1-C_7$ alkyl (but not cycloalkyl), phenyl, or phenyl substituted with hydroxy, nitro, cyano, amino, $C_1-C_6$ alkoxy, or halogen, or when A is 1 and $Z_1$ is —$C(R_4)(R_5)$— wherein m is 1, 2, or 3, and $R_1$ is straight or branched chain $C_1-C_7$ alkyl (but not cycloalkyl), phenyl, or phenyl substituted with hydroxy, nitro, cyano, amino, $C_1-C_6$ alkoxy, or halogen, or when $Z_2$ is phenylene and A is 1 and $Z$, is —$C(R_4)(R_5)$— wherein m is 1, 2, or 3 and $R_1$ is straight or branched chain $C_1-C_7$ alkyl (but not cycloalkyl), phenyl, or phenyl substituted with hydroxy, nitro, cyano, amino, $C_1-C_6$ alkoxy, or halogen, or when $Z_2$ is —$C(R_7)(R_8)$— wherein n is 1, 2, or 3, each occurrence of $R_7$ and $R_8$ is independently straight or branched chain $C_1-C_6$ alkyl or halogen and $R_2$ is $C_1-C_6$ alkoxy or phenyl substituted with nitro), cyano, amino, halogen, $C_1-C_6$ alkyl, $C_1-C_6$ perfluoroalkyl, $C_1-C_6$ perfluoroalkoxy, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$ alkoxy, mono- or di($C_1-C_6$ alkyl)amino, or amino($C_1-C_6$ alkyl); phenyoxy phenyl where each phenyl may be independently unsubstituted, mono-, di- or trisubstituted with one or more of hydroxy, nitro, cyano, amino, halogen, sulfonamide, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$ alkoxy, mono- or di($C_1-C_6$ alkyl)amino, or amino($C_1-C_6$ alkyl); phenyl or heteroaryl piperazine where the phenyl or heteroaryl ring may be independently unsubstituted, mono-, di- or trisubstituted with one or more of hydroxy, nitro, cyano, amino, halogen, sulfonamide, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$alkoxy, mono- or di($C_1-C_6$ alkyl)amino, or mono- or di($C_1-C_6$ alkyl)amino($C_1-C_6$ alkyl);

$R_3$ is hydrogen; straight or branched chain $C_1-C_7$ alkyl, in which the branched alkyl chains may form a 3–7 member heteroalkyl or alkyl ring;

$Z_1$ is

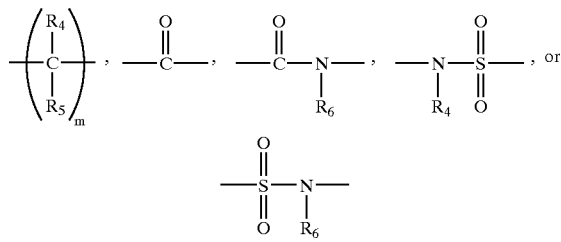

wherein
A is 0 or 1;
each occurrence of $R_4$ and $R_5$ is independently hydrogen, straight or branched chain $C_1-C_6$ alkyl, sulfonamide, or halogen;
m is 0, 1, or 2; and
$R_6$ is hydrogen; straight or branched chain $C_1-C_6$ alkyl; phenyl which may be unsubstituted, mono-, di- or trisubstituted with one or more of hydroxy, nitro, cyano, amino, halogen, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$alkoxy, mono- or di($C_1-C_6$ alkyl)amino, or amino($C_1-C_6$ alkyl); or heteroaryl which may be unsubstituted, mono-, di- or trisubstituted with one or more of hydroxy, nitro, cyano, amino, halogen, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$alkoxy, mono- or di($C_1-C_6$ alkyl)amino, or amino($C_1-C_6$ alkyl); and $Z_2$ is a divalent linking group selected from para-phenylene, meta-phenylene, ortho-phenylene, or naphthylene, and

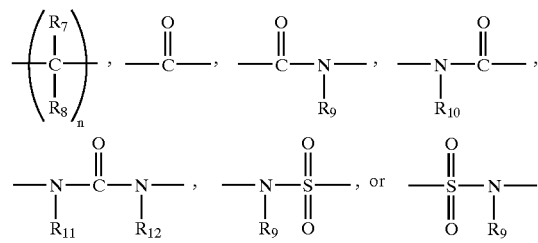

wherein
each occurrence of $R_7$ and $R_8$ is independently straight or branched chain $C_1-C_6$ alkyl, sulfonamide, or halogen;
n is 0,1, 2, or 3; and
$R_9-R_{12}$ are each independently hydrogen; straight or branched chain $C_1-C_6$ alkyl; phenyl which may be unsubstituted, mono-, di- or trisubstituted with one or more of hydroxy, nitro, cyano, amino, halogen, $C_1-C_6$ alkyl, $C_1-C_6$ alkoxy, $(C_1-C_6)$-alkyl-oxy-$(C_1-C_6)$ alkoxy, mono- or di($C_1-C_6$ alkyl)amino, or amino ($C_1-C_6$ alkyl); or heteroaryl which may be unsubstituted, mono-, di- or trisubstituted with one or more of hydroxy, nitro, cyano, amino, halogen, $C_1-C_6$ alkyl, $C_1-C_6$ alkoxy,$(C_1-C_6)$-alkyl-oxy-$(C_1-C_6)$ alkoxy, mono- or di($C_1-C_6$ alkyl)amino, or amino ($C_1-C_6$ alkyl).

In another embodiment, a pharmaceutical composition comprises a therapeutically effective amount of a compound of Formula 1 and a pharmaceutically acceptable carrier.

In still another embodiment, a method of treating a kinase-implicated disorder in a mammal comprises administration to the mammal of a pharmaceutical composition comprising a therapeutically effective amount of a compound of Formula 1 and a pharmaceutically acceptable carrier.

In another embodiment, a method for identifying a kinase comprises contacting an organism, cell, or preparation comprising the kinase with a compound of Formula 1, and detecting modulation of the kinase activity.

DETAILED DESCRIPTION

Figure 1:
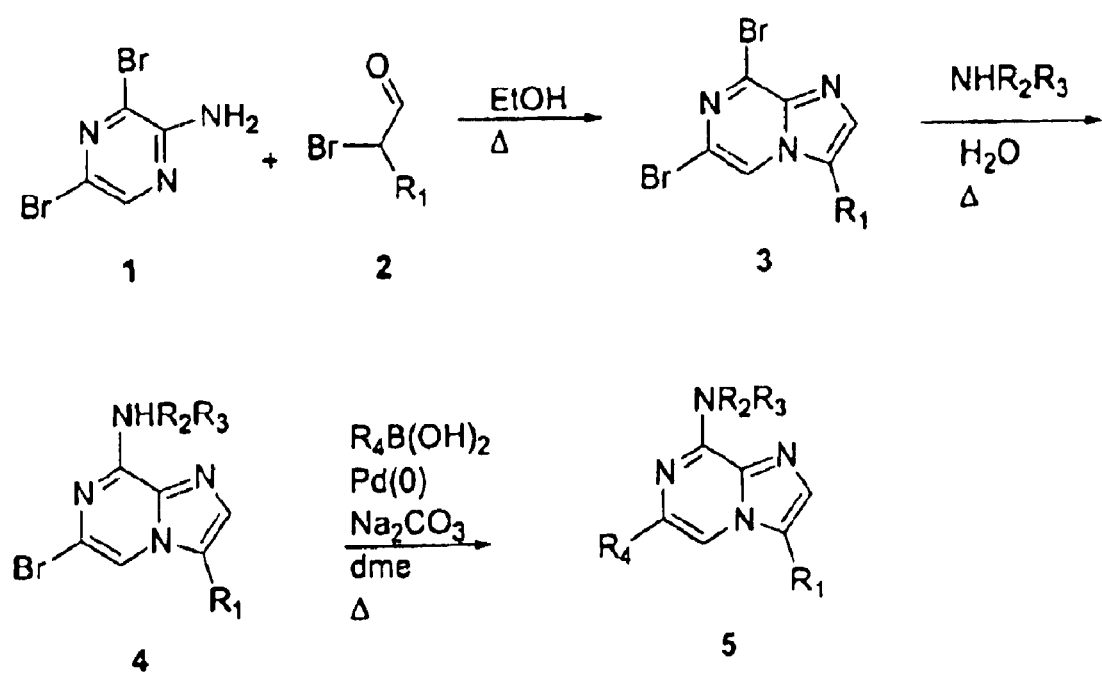
FIG. 1 is a schematic illustrating one synthesis of the present compounds.

The compounds of Formula 1 are novel compounds belonging to the family of imidazo[1,2-a]pyrazines. Without wishing to be bound to any particular theory, it is believed that the interaction of the compounds of Formula 1 with a kinase (i.e., one or more kinases) results in modulation of the activity of the kinase(s). The compounds of Formula 1 are thus expected to have therapeutic application in mammalian kinase-implicated conditions. As used herein, "modulation" refers to a change in kinase activity as a direct or indirect response to the presence of a compound of Formula 1, relative to the activity of the kinase in the absence of the compound. The change may be an increase in activity or a decrease in activity, and may be due to the direct interaction of the compound with the kinase, or due to the interaction of the compound with one or more other factors that in turn affect kinase activity. For example, the presence of the compound may increase or decrease kinase activity by directly binding to the kinase, by causing (directly or indirectly) another factor to increase or decrease the kinase activity, or by (directly or indirectly) increasing or decreasing the amount of kinase present in the cell or organism.

In one preferred embodiment, novel imidazo[1,2-a]pyrazines may comprise compounds of general Formula 2:

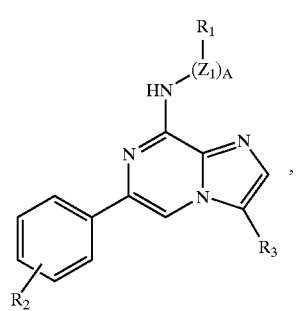

(2)

the pharmaceutically acceptable salts, hydrates, solvates, crystal forms, diastereomers, prodrugs, or mixtures thereof.

In Formula 2, $R_1$ is hydrogen; cyclo-($C_3$–$C_6$ alkyl)-methyl; straight or branched chain $C_1$–$C_7$ alkyl, in which the branched alkyl chains are allowed to also form a 3–7 member heteroalkyl or alkyl ring; sulfonamide; $C_1$–$C_6$ alkoxy; ($C_1$–$C_6$)-alkyl-oxy-($C_1$–$C_6$)alkoxy; mono- or di($C_1$–$C_6$ alkyl)amino, or mono- or di($C_1$–$C_6$ alkyl)amino ($C_1$–$C_6$ alkyl); or phenyl or heteroaryl ring which may be unsubstituted, mono-, di- or trisubstituted with one or more of hydroxy, nitro, cyano, amino, sulfonamide, halogen, $C_1$–$C_6$ alkyl, $C_1$–$C_6$ perfluoroalkyl, $C_1$–$C_6$ perfluoroalkoxy, $C_1$–$C_6$ alkoxy, mono- or di($C_1$–$C_6$ alkyl)amino, or mono- or di($C_1$–$C_6$ alkyl)amino($C_1$–$C_6$ alkyl).

$R_2$ in Formula 2 is straight or branched chain $C_1$–$C_7$ alkyl, in which the branched alkyl chains are allowed to also form a 3–7 member heteroalkyl or alkyl ring; cyclo-($C_3$–$C_6$ alkyl)-methyl; $C_1$–$C_6$ alkoxy except when A is 0 and $R_1$ is straight or branched chain $C_1$–$C_7$ alkyl (but not cycloalkyl), phenyl, or phenyl substituted with hydroxy, nitro, cyano, amino, $C_1$–$C_6$ alkoxy, or halogen, or when A is 1 and $Z_1$ is —C($R_4$)($R_5$)— wherein m is 1, 2, or 3 and $R_1$ is straight or branched chain $C_1$–$C_7$ alkyl (but not cycloalkyl), phenyl, or phenyl substituted with hydroxy, nitro, cyano, amino, $C_1$–$C_6$ alkoxy, or halogen; ($C_1$–$C_6$)-alkyl-oxy-($C_1$–$C_6$)alkoxy; phenyl or heteroaryl which may be unsubstituted, mono-, di- or trisubstituted with one or more of hydroxy, nitro, (except when A is 0 and $R_1$ is straight or branched chain $C_1$–$C_7$ alkyl (but not cycloalkyl), phenyl, or phenyl substituted with hydroxy, nitro, cyano, amino, $C_1$–$C_6$ alkoxy, or halogen, or when A is 1 and $Z_1$ is —C($R_4$)($R_5$)— wherein m is 1, 2, or 3 and $R_1$ is straight or branched chain $C_1$–$C_7$ alkyl (but not cycloalkyl), phenyl, or phenyl substituted with hydroxy, nitro, cyano, amino, $C_1$–$C_6$ alkoxy, or halogen)cyano, amino, halogen, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$) alkoxy, mono- or di($C_1$–$C_6$ alkyl)amino, amino($C_1$–$C_6$ alkyl); phenyoxy phenyl where each phenyl may be independently unsubstituted, mono-, di- or trisubstituted with one or more of hydroxy, nitro, cyano, amino, halogen, sulfonamide, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$) alkoxy, mono- or di($C_1$–$C_6$ alkyl)amino, or amino($C_1$–$C_6$ alkyl); or phenyl or heteroaryl piperazine where the phenyl or heteroaryl ring may be independently unsubstituted, mono-, di- or trisubstituted with one or more of hydroxy, nitro, cyano, amino, halogen, sulfonamide, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono- or di($C_1$–$C_6$ alkyl)amino, or mono- or di($C_1$–$C_6$ alkyl)amino ($C_1$–$C_6$ alkyl).

$R_3$ in Formula 2 may be hydrogen; straight or branched chain $C_1$–$C_7$ alkyl, in which the branched alkyl chains can also form a 3–7 member heteroalkyl or alkyl ring.

A in Formula 2 is 0 or 1.

$Z_1$ in Formula 2 is

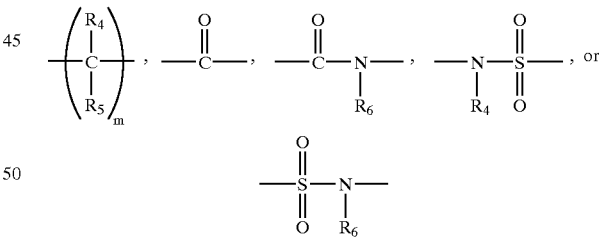

wherein each occurrence of $R_4$ and $R_5$ is independently hydrogen, straight or branched chain $C_1$–$C_6$ alkyl, sulfonamide, or halogen;

m is 1, 2, or 3; and $R_6$ is hydrogen; straight or branched chain $C_1$–$C_6$ alkyl; phenyl, which may be unsubstituted, mono-, di- or trisubstituted with one or more of hydroxy, nitro, cyano, amino, halogen, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono- or di($C_1$–$C_6$ alkyl)amino, or amino($C_1$–$C_6$ alkyl); or heteroaryl, which may be unsubstituted, mono-, di- or trisubstituted with one or more of hydroxy, nitro, cyano, amino, halogen, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono- or di($C_1$–$C_6$ alkyl)amino, or amino($C_1$–$C_6$ alkyl).

In another preferred embodiment, the novel imidazo[1,2-a]pyrazines comprise compounds of general Formula 3:

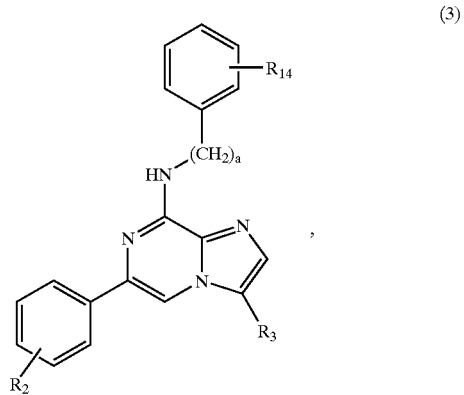

(3)

the pharmaceutically acceptable salts, hydrates, solvates, crystal forms, diastereomers, prodrugs, or mixtures thereof.

In Formula 3, a is 0, 1, 2 or 3. $R_{14}$ is hydrogen; cyclo-($C_3$–$C_6$ alkyl)-methyl; straight or branched chain $C_1$–$C_6$ alkyl, in which the branched alkyl chains may form a 3–7 member heteroalkyl or alkyl ring; sulfonamide; $C_1$–$C_6$ alkoxy; ($C_1$–$C_6$)-alkyl-oxy-($C_1$–$C_6$)alkoxy; mono- or di($C_1$–$C_6$ alkyl)amino, mono- or di($C_1$–$C_6$ alkyl)amino ($C_1$–$C_6$ alkyl); or phenyl or heteroaryl ring, which may be unsubstituted, mono-, di- or trisubstituted with one or more of hydroxy, nitro, cyano, amino, sulfonamide, halogen, $C_1$–$C_6$ alkyl, $C_1$–$C_6$ perfluoroalkyl, $C_1$–$C_6$ perfluoroalkoxy, $C_1$–$C_6$ alkoxy, mono- or di($C_1$–$C_6$ alkyl)amino, or mono- or di($C_1$–$C_6$ alkyl)amino($C_1$–$C_6$ alkyl).

$R_2$ in Formula 3 is straight or branched chain $C_1$–$C_6$ alkyl, in which the branched alkyl chains may form a 3–7 member heteroalkyl or alkyl ring; cyclo-($C_3$–$C_6$ alkyl)-methyl; $C_1$–$C_6$ alkoxy except where $R_1$ is hydrogen, $C_1$–$C_6$ alkoxy, or phenyl substituted with nitro; ($C_1$–$C_6$)-alkyl-oxy-($C_1$–$C_6$) alkoxy; phenyl or heteroaryl, which may be unsubstituted, mono-, di- or trisubstituted with one or more of hydroxy, nitro, cyano, amino, halogen, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono- or di($C_1$–$C_6$ alkyl)amino, or amino($C_1$–$C_6$ alkyl); phenyoxy phenyl, in which each phenyl may be independently unsubstituted, mono-, di- or trisubstituted with one or more of hydroxy, nitro (except where $R_1$ is hydrogen, $C_1$–$C_6$ alkoxy, or phenyl substituted with nitro), cyano, amino, halogen, sulfonamide, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono- or di($C_1$–$C_6$ alkyl)amino, or amino($C_1$–$C_6$ alkyl); or phenyl or heteroaryl piperazine, in which the phenyl or heteroaryl ring may be independently unsubstituted, mono-, di- or trisubstituted with one or more of hydroxy, nitro, cyano, amino, halogen, sulfonamide, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono- or di($C_1$–$C_6$ alkyl)amino, or mono- or di($C_1$–$C_6$ alkyl)amino($C_1$–$C_6$ alkyl).

$R_3$ is hydrogen; straight or branched chain $C_1$–$C_6$ alkyl, in which the branched alkyl chains may form a 3–7 member heteroalkyl or alkyl ring.

As used herein, when any variable occurs more than one time in the formulas, its definition on each occurrence is independent of its definition at every other occurrence. In accordance with the usual meaning of "a" and "the" in patents, reference to "a" kinase or "the" kinase is inclusive of one or more kinases.

By "heteroaryl" is meant aromatic systems containing at least one heteroatom, for example, oxygen, nitrogen, sulfur, and the like, as well as combinations comprising at least one of the foregoing heteroatoms. Suitable heteroaryl groups include, for example (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, and the like.

By "heteroalkyl" is meant an aliphatic ring containing at least 1 carbon atom in addition to 1–3 heteroatoms independently selected from oxygen, sulfur, or nitrogen, and the like, as well as combinations comprising at least one of the foregoing heteroatoms.

By "sulfonamide" is meant —S(O)$_2$N— in either S-linked or N-linked orientation, wherein the nitrogen atom can be unsubstituted; or mono- or disubstituted with cyclo-($C_3$–$C_6$ alkyl)-methyl or straight or branched chain $C_1$–$C_7$ alkyl, in which the branched alkyl chains may form a 3–7 member alkyl or heteroalkyl ring.

By "piperazine" is meant unsubstituted piperazine, as well as piperazines independently substituted on 1–4 carbon atoms with hydroxy, cyano, amino, halogen, $C_1$–$C_6$ alkyl, $C_1$–$C_6$ perfluoroalkyl, $C_1$–$C_6$ perfluoroalkoxy, $C_1$–$C_6$ alkoxy, mono- or di($C_1$–$C_6$ alkyl)amino, mono- or di($C_1$–$C_6$ alkyl)amino($C_1$–$C_6$ alkyl), or sulfonamide.

By "$C_1$–$C_6$ alkyl" is meant straight or branched chain alkyl groups or cycloalkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Preferred $C_1$–$C_6$ alkyl groups are methyl, ethyl, propyl, butyl, cyclopropyl, cyclopropylmethyl, cyclohexyl, cycloheptyl, and norbornyl.

By "$C_1$–$C_6$ alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, 3-methylpentoxy, and the like. Preferred alkoxy groups herein are $C_1$–$C_4$ alkoxy groups.

The term "halogen" includes fluorine, chlorine, bromine, and iodine.

If the compounds of Formula 1 have asymmetric centers, then Formula 1 includes all of the optical isomers and mixtures thereof. In addition, compounds with carbon-carbon double bonds may occur in Z- and E-forms, with all isomeric forms of the compounds being included. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. Where a compound of Formula 1 exists in various tautomeric forms, the invention is not limited to any one of the specific tautomers, and includes all tautomeric forms of the compound.

Representative compounds of the present invention, which are encompassed by Formula 1, include, but are not limited to their pharmaceutically acceptable acid addition salts. Non-toxic "pharmaceutically acceptable salts" include, but are not limited to salts with inorganic acids, such as hydrochlorate, phosphate, diphosphate, hydrobromate, sulfate, sulfinate, nitrate, or like salts; or salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0–4, and like salts. Similarly, pharmaceutically acceptable cations include, but are not limited to sodium, potassium, calcium, aluminum, lithium, and ammonium.

In addition, if the compound of Formula 1 is obtained as an acid addition salt, the free base can be obtained by basifying a solution of the acid salt. Conversely, if the product is a free base, an addition salt, particularly a pharmaceutically acceptable addition salt, it may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts encompassed by Formula I.

Prodrugs of the compounds of Formula 1 are also within the scope of the present invention, for example acylated prodrugs of the compounds of Formula 1. Those skilled in the art will recognize various synthetic methodologies that may be used to prepare non-toxic pharmaceutically acceptable acylated and other prodrugs of the compounds encompassed by Formula 1.

Methods for obtaining the compounds described herein are known to those of ordinary skill in the art, suitable procedures being described, for example, in the references cited herein.

As mentioned above, it is believed that the interaction of the compounds of Formula 1 with one or more kinases results in modulation of the activity of the one or more kinases. Suitable kinases include but are not limited to tyrosine kinases and serine/threonine kinases, which may be classified as including the AGC group (cyclic nucleotide regulated family) of protein kinases, which includes the cyclic nucleotide regulated protein kinase family (e.g., PKA and PKG), the diacylglycerol-activated/phospholipid-dependent family protein kinase C family (e.g., PKC), the PKA and PKC-related family (e.g., RAC and Akt), the kinases that phosphorylate G protein-coupled receptors family, the budding yeast AGC-related protein kinase family, the kinases that phosphorylate ribosomal protein S6 family, the budding yeast DBF2/20 family, the flowering plant PVPK1 protein kinase homolog family, and other AGC related kinase families.

The CaMK (calcium calmodulin dependent) group of protein kinases includes kinases regulated by $Ca^{2+}$/CaM and close relatives family, the KIN1/SNF1/Nim1 family, and other related CaMK related kinase families. The CMGC group (named because it includes the cyclin-dependent kinases) includes the cyclin-dependent kinases (e.g., CDKs) and close relatives family, the ERK (e.g., MAP) kinase family, the glycogen synthase 3 (e.g., GSK3) family, the casein kinase II family, the Clk family and other CMGC kinases.

The PTK group of protein kinases includes protein-tyrosine kinases that may be nonmembrane-spanning or membrane-spanning tyrosine kinases. The PTK group of protein kinases includes the Src family, the Tek/Atk family, the Csk family, the Fes (Fps) family, the Abl family, the Syk/ZAP70 family, the Ttk2/Jak1 family, the Ack family, the focal adhesion kinase (Fak) family, the epidermal growth factor receptor family, the Eph/Elk/Eck receptor family, the Axl family, the Tie/Tek family, the platelet-derived growth factor receptor family, the fibroblast growth factor receptor family, the insulin receptor family, the LTK/ALK family, the Ros/Sevenless family, the Trk/Ror family, the DDR/TKT family, the hepatocyte growth factor receptor family, the nematode Kin15/16 family and other PTK kinase families.

The OPK group (other protein kinases) includes the Polo family, the MEK/STE7 family, the PAK/STE20 family, the MEKK/STE11 family, the NimA family, the wee1/mik1 family, the kinases involved in transcriptional control family, the Raf family, the Activin/TGFb receptor family, the flowering plant putative receptor kinases and close relatives family, the PSK/PTK leucine zipper domain family, the casein kinase I family, the PKN prokaryotic protein kinase family and other OPK protein kinase families. A large number of kinases are found in G. Hardie et al., *Protein Kinase Facts Book* 0-12-324719-5 (1995).

Accordingly, a method of treating a kinase-implicated disease or condition in a mammal, preferably a human, comprises administration to the mammal of a pharmaceutical composition comprising a therapeutically effective amount of a compound of Formula 1 and a pharmaceutically acceptable carrier. As used herein "therapeutically effective" includes alleviation of disease, disease symptoms, preventative, and prophylactic treatment.

Kinases are implicated in a large variety of diseases, as certain mutations in protein kinases can lead to activation of pathways causing, for example, the production of tumors, while other mutations in protein kinases block pathways and prevent a response. Some diseases that are linked to mutations in protein kinases are listed in the KinMutBase database (http://www.uta.fi/imt/bioinfo/KinMutBase/) (Stenberg et al., Nucleic Acids Research, Vol. 28, pp. 369–372, 2000). Diseases caused by protein kinase mutations include X-linked agammaglobulinemia (XLA), and non-insulin dependent diabetes mellitus (NIDDM), and severe combined immunodeficiency (SCID). Mutations related to tumor development have been liked to such diseases as Hirschprung's disease, multiple endocrine neoplasia type 2 (MEN2) a and b, medullary thyroid carcinoma (FMTC), papillary renal carcinoma (HPRC), and Peutz-Jeghers syndrome.

Mutations in growth factor receptor kinases are linked to diseases such as mastocytosis, systemic mast cell disease, piebaldism, hypochondroplasia, thanatophoric dysplasia, and skeletal dysplasia. Other protein kinase-linked diseases include Coffin-Lowry syndrome, congenital insensitivity to pain with anhidrosis (CIPA), hypertension, vascular dysplasia, errors in vascular morphogenesis, and X-linked mental retardation. Mutations in protein kinases have also been linked to neurodegenerative diseases such as amyotrophic lateral sclerosis (ALS) and Alzheimer's disease (AD).

Other diseases associated with protein kinases include Gaucher disease, hypochromic anemia, granulomatous disease, ataxia-telangiectasia, familial hypercholesterolemia, certain types of muscular dystrophy such as Driefuss-Emory type, cystic fibrosis, type 1 hyperlipoproteinemia, Treacher Collins Franceschetti syndrome 1, Tay-Sachs disease, type 1 neurofibromatosis, adenomatous polyposis of the colon, X-linked ichthyosis, and Beckwith-Weidemann Syndrome.

Altered PKA (cyclic AMP-dependent protein kinase) expression is implicated in a variety of disorders and diseases including cancer, thyroid disorders, diabetes, atherosclerosis, and cardiovascular disease. Altered MAP (mitogen-activated protein) kinase expression is implicated in a variety of disease conditions including cancer, inflammation, immune disorders, and disorders affecting growth and development. RTKs (receptor tyrosine kinases), CDKs and STKs (serine/threonine kinases) have all been implicated in a host of pathogenic conditions including, significantly, large number of diverse cancers. Others pathogenic conditions that have been associated with PTKs include, psoriasis, hepatic cirrhosis, diabetes, atherosclerosis, angiogenesis, restinosis, ocular diseases, rheumatoid arthritis and other inflammatory disorders, autoimmune disease, and a variety of renal disorders.

Preferably, the conditions, diseases and/or disorders that can be affected using compounds of Formula 1 and compositions comprising such compounds include, but are not limited to, psoriasis, cancer (for example, chronic myelogenous leukemia, gastrointestinal stromal tumors, non-small cell lung cancer, breast cancer, ovarian cancer, recurrent ovarian cancer, prostate cancer such as hormonal refractory prostate cancer, kidney cancer, head and neck cancer, or colorectal cancer), immunoregulation (graft rejection), atherosclerosis, rheumatoid arthritis, Parkinson's disease, Alzheimer's disease, diabetes (for example insulin resistance or diabetic retinopathy), septic shock, and the like.

In a preferred embodiment, the condition is cancer. A method of treating cancer comprising administering to a mammal in need thereof a therapeutically effective amount of a compound of Formulas 1, 2, or 3 and a therapeutically effective amount of an antitumor therapeutic. Treatment with the antitumor therapeutic may be prior to treatment with the inventive compounds, during treatment, following treatment with the compounds, or a combination thereof. Suitable antitumor therapeutics are known, and are preferably a chemotherapeutic agent, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

In another embodiment, pharmaceutical compositions comprising at least one compound of Formula 1, together with one or more non-toxic, pharmaceutically acceptable carriers and/or diluents and/or adjuvants, and if desired other active ingredients. Such pharmaceutical compositions include packaged pharmaceutical compositions for treating disorders responsive to modulation of kinase activity. A packaged pharmaceutical composition includes a container holding a therapeutically effective amount of at least compound of Formula 1 and instructions (e.g., labeling) indicating that the contained composition is to be used for treating a disorder responsive to kinase modulation in the patient. Those of ordinary skill in the art will also recognize a wide variety of non-toxic pharmaceutically acceptable solvents that may be used to prepare solvates of the compounds of the invention, such as water, ethanol, mineral oil, vegetable oil, and dimethylsulfoxide (DMSO).

The compounds of Formula 1 may be administered orally, topically, parenterally, by inhalation or spray or rectally in dosage unit formulations containing conventional non-toxic pharmaceutically acceptable carriers, adjuvants, and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. The pharmaceutical compositions containing compounds of Formula 1 may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents, such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example sweetening, flavoring, and coloring agents, may also be present.

Suitable pharmaceutical compositions for therapeutic use may also be in the form of oil-in-water emulsions. The oily phase may be a vegetable oil, for example olive oil or arachis oil, or a mineral oil, for example liquid paraffin, or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol, or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula 1 may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of Formula 1 may be administered parenterally in a sterile medium. The drug, depending on the vehicle and concentration used, can either be suspended or dissolved in the vehicle. Advantageously, adjuvants such as local anesthetics, preservatives, and buffering agents can be dissolved in the vehicle.

For administration to non-human animals, the composition may also be added to the animal feed or drinking water. It is convenient to formulate these animal feed and drinking water compositions so that the animal takes in an appropriate quantity of the composition along with its diet. It is also convenient to present the composition as a premix for addition to the feed or drinking water.

Dosage levels of the order of from about 0.1 milligram to about 140 milligram per kilogram of body weight per day are useful in the treatment of the above-indicated conditions (about 0.5 milligram to about 7 gram per human patient per day). The amount of active ingredient that may be combined with the carrier materials to produce a single dosage form will vary depending upon the host treated and the particular mode of administration. Dosage unit forms will generally contain between from about 1 mg to about 500 milligram of an active ingredient.

Frequency of dosage may also vary depending on the compound used and the particular disease treated. However, for treatment of most disorders, a dosage regimen of 4 times daily or less is preferred. For the treatment of eating disorders, including obesity, a dosage regimen of 1 or 2 times daily is particularly preferred. For the treatment of impotence a single dose that rapidly reaches effective concentrations is desirable. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding, and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (*Journal of Chromatography B* 1996, volume 677, pages 1–27).

Compound half-life is inversely proportional to the frequency of dosage of a compound. In vitro half-lives of compounds may be predicted from assays of microsomal half-life as described by Kuhnz and Gieschen (*Drug Metabolism and Disposition* 1998, volume 26, pages 1120–1127).

In another embodiment, the compounds of Formula 1 are also useful as probes for the localization of kinases of therapeutic interest, that is, for both in vivo and in vitro identification and isolation the specific proteins to which it binds. A method for identifying a kinase comprises contacting an organism, cell, or preparation comprising the kinase with compound or salt according to Formulas 1, 2, or 3, and detecting modulation of an activity of the kinase. Suitable methods for detecting kinase modulation are known, for example those described herein.

The invention is further illustrated by the following non-limiting examples.

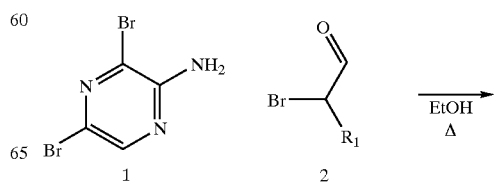

EXAMPLE 1

Synthesis of Compounds of Formula 1 (FIG. 1)

6,8-dibromoimidazo[1,2-a]pyrazine (3). A solution of 1.00 equivalents (eq.) of 3,5-dibromo-2-aminopyrazine 1 in ethanol is treated with 2.00 eq. of α-bromoaldehyde 2 at room temperature (RT) and heated for 48 hours (hr). The solvent is removed under reduced pressure and the residue is triturated with diethyl ether and filtered to give the HBr salt 3.

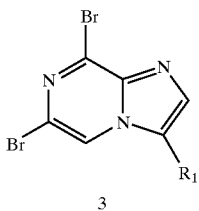

8-Amino-6-bromoimidazo[1,2-a]pyrazine (4). Procedure 1: A mixture of

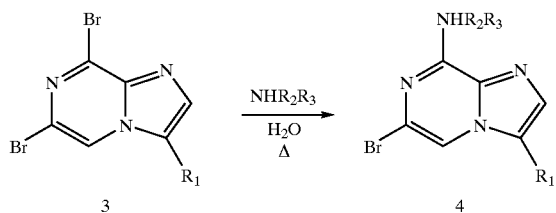

1.00 eq. of 6,8-imidazo[1,2-a]pyrazine 3 in 28% ammonia/water solution or 40% aqueous methyl amine is heated to between 80 to 90° C. for 24 hr. The resulting mixture is partitioned between $CH_2Cl_2$ and $H_2O$. The aqueous layer is extracted with $CH_2Cl_2$ and the combined organic extracts are dried over $Na_2SO_4$. The solvent is removed under reduced pressure and the resulting residue is crystallized from ethanol to yield 4.

Procedure 2: A solution of 1.00 eq. of 6,8-imidazo[1,2-a]pyrazine 3 in N,N-dimethylacetamide is treated with 2.00 eq. of benzylamine and 3.00 eq. of $K_2CO_3$. The resulting mixture is heated to 100° C. for 24 to 48 hours, cooled to RT and partitioned between $H_2O/CH_2Cl_2$. The aqueous layer is extracted with $CH_2Cl_2$ and combined organic extracts are dried over $Na_2SO_4$. The solvent is removed under reduced pressure and the resulting residue is purified by flash chromatography (3:7 ethyl acetate (EtOAc)/Hexanes) to yield 4.

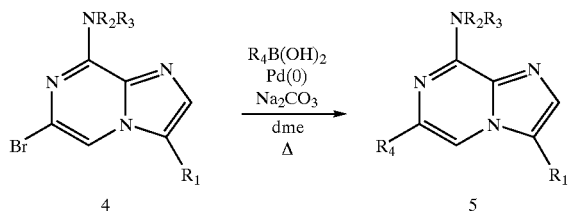

8-Amino-6-aryl-imidazo[1,2-a]pyrazine (5). A mixture of 1.00 eq. of 8-amino-6-bromoimidazo[1,2-a]pyrazine, 3.00 eq. of $R_4$-sustituted boronic acid, and 0.10 eq. of Pd $(PPh_{3b})_4$, in 6.00 eq. of 1N $Na_2CO_3$/dme is heated to 90° C. for 24 hr. The mixture is cooled to RT and partitioned between 10% acetic acid (AcOH)/$CH_2Cl_2$. The aqueous phase is extracted with $CH_2Cl_2$ and combined extracts are dried over $Na_2SO_4$. The solvent is removed under reduced pressure and the resulting residue is purified by flash chromatography (1–5% 2M $NH_3$/methanol/$CH_2Cl_2$) to yield 5.

EXAMPLE 2

Figure 2:
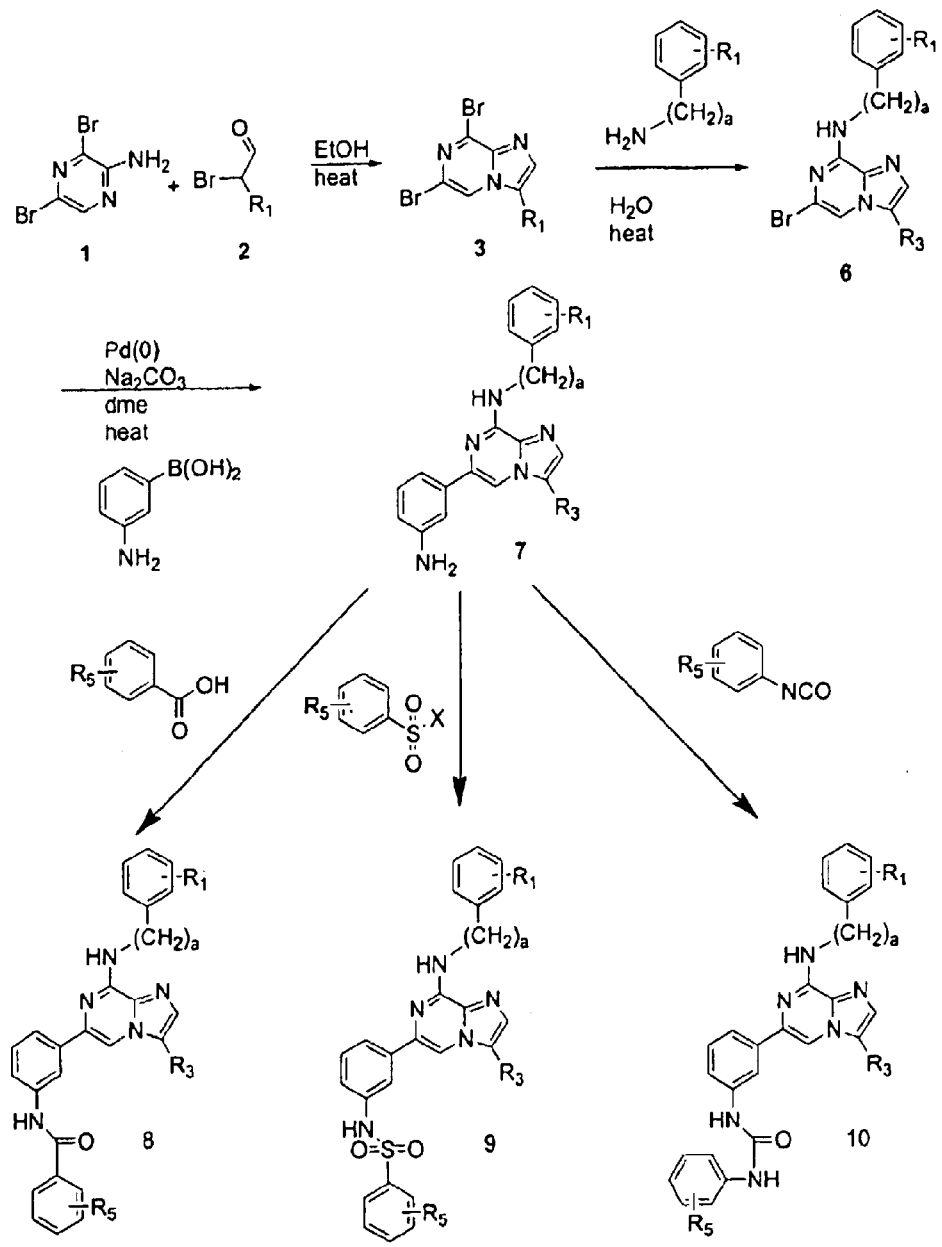
FIG. 2 is a schematic illustrating another synthesis of the present compounds.

Synthesis of Compounds of Formula 1b (FIG. 2).

8-Amino-6-aryl-imidazo[1,2-a]pyrazine (6). A mixture of 1.00 eq. of 8-amino-6-bromoimidazo[1,2-a]pyrazine, 3.00 eq. of $R_4$-sustituted boronic acid, and 0.10 eq. of Pd $(PPh_3)_4$, in 4.00 eq. of 1N $Na_2CO_3$/dme is heated to 90° C. for 24 hr. The mixture is cooled to RT and partitioned between EtOAc/saturated $NaHCO_3$. The aqueous phase is extracted with EtOAc and the combined extracts are dried over $Na_2SO_4$. The solvent is removed under reduced pressure and the resulting residue is purified by flash chromatography (1–5% 2M $NH_3$/methanol/EtOAc) to yield 6.

N-[3-(8-Benzylamino-imidazo[1,2-a]pyrazin-6-yl)-phenyl]-benzamide (8). A solution of 1.00 eq. of 8-amino-6-aryl-imidazo[1,2-a]pyrazine in toluene/DMA is treated dropwise with 1.00 eq. of aryl acid chloride and stirred at RT for 10 hr. The resulting mixture is partitioned between EtOAc/saturated $NaHCO_3$. The aqueous phase is extracted with EtOAc and the combined extracts are dried over $Na_2SO_4$. The solvent is removed under reduced pressure and the resulting residue is purified by flash chromatography (1–5% methanol/EtOAc) to yield 8.

N-[3-(8-Benzylamino-imidazo[1,2-a]pyrazin-6-yl)-phenyl]-benzenesulfonamide (9). A solution of 1.00 eq. of 8-amino-6-aryl-imidazo[1,2-a]pyrazine in 5% N-methyl morpholine (NMM)/toluene is treated dropwise with 1.1 eq of aryl sulfonyl chloride and heated to 50° C. for 8 h. The solution is cooled to RT and partitioned between EtOAc/saturated $NaHCO_3$. The aqueous phase is extracted with EtOAc and the combined extracts are dried over $Na_2SO_4$. The solvent is removed under reduced pressure and the resulting residue is purified by flash chromatography ((1–5% methanol/EtOAc) to yield 9.

1-[3-(8-Benzylamino-imidazo[1,2-a]pyrazin-6-yl)-phenyl]-3-phenyl-urea (10). A solution of 1.00 eq. of 8-amino-6-aryl-imidazo[1,2-a]pyrazine in 5% NMM/toluene is treated dropwise with 1.0 eq of aryl isocyanate and heated to 60° C. for 8 hr. The solution is cooled to RT and partitioned between EtOAc/saturated $NaHCO_3$. The aqueous phase is extracted with EtOAc and the combined extracts are dried over $Na_2SO_4$. The solvent is removed under reduced pressure and the resulting residue is purified by flash chromatography (1–5% 2M $NH_3$/MeOH/EtOAc) to yield 10.

EXAMPLE 3

The following compounds were prepared in accordance with FIGS. 1 and 2 using the above procedures.
 (a) 1-(4-Chloro-phenyl)-3-[3-(8-methylamino-imidazo[1,2-a]pyrazin-6-yl)-phenyl]-urea, MF=$C_{20}H_{17}ClN_6O$, MW=392.84 Mass Spec m/z (M$^+$+1) 393.06.
 (b) 1-(4-Chloro-phenyl)-3-[3-(8-phenylamino-imidazo[1,2-a]pyrazin-6-yl)-phenyl]-urea, MF=$C_{25}H_{19}ClN_6O$ MW=454.91 Mass Spec m/z (M$^+$+1) 455.04.
 (c) 1-(4-Chloro-phenyl)-3-{3-[8-(4-chloro-phenylamino)-imidazo[1,2-a]pyrazin-6-yl]-phenyl}-urea, MF=$C_{25}H_{18}Cl_2N_6O$, MW–489.36 Mass Spec m/z (M$^+$+1) 489.20.

(d) 1-(4-Chloro-phenyl)-3-{3-[8-(3-chloro-phenylamino)-imidazo[1,2-a]pyrazin-6-yl]-phenyl}-urea, MF=$C_{25}H_{18}Cl_2N_6O$, MW=489.36 Mass Spec m/z (M$^+$–1) 489.13.

(e) 1-(4-Chloro-phenyl)-3-{3-[8-(2-chloro-phenylamino)-imidazo[1,2-a]pyrazin-6-yl]-phenyl}-urea, MF=$C_{25}H_{18}Cl_2N_6O$, MW=489.36 Mass Spec m/z (M$^+$+1) 489.04.

(f) 1-(4-Chloro-phenyl)-3-{3-[8-(pyridin-3-ylamino)-imidazo[1,2-a]pyrazin-6-yl]-phenyl}-urea, MF=$C_{24}H_{18}ClN_7O$, MW=455.90 Mass Spec m/z (M$^+$+1) 456.07.

(g) 1-{3-[8-(4-Chloro-benzylamino)-imidazo[1,2-a]pyrazin-6-yl]-phenyl}-3-(4-chloro-phenyl)-urea, MF=$C_{26}H_{20}Cl_2N_6O$, MW=503.38 Mass Spec m/z (M$^+$+1) 503.04.

(h) 1-{3-[8-(3-Chloro-benzylamino)-imidazo[1,2-a]pyrazin-6-yl]-phenyl}-3-(4-chloro-phenyl)-urea, MF=$C_{26}H_{20}Cl_2N_6O$, MW=503.38 Mass Spec m/z (M$^+$+1) 503.01.

(i) 1-{4-[8-(4-Chloro-benzylamino)-imidazo[1,2-a]pyrazin-6-yl]-phenyl}-3-(4-chloro-phenyl)-urea, MF=$C_{26}H_{20}Cl_2N_6O$, MW=503.38 Mass Spec m/z (M$^+$+1) 503.01.

(j) 1-{4-[8-(3-Chloro-benzylamino)-imidazo[1,2-a]pyrazin-6-yl]-phenyl}-3-(4-chloro-phenyl)-urea, MF=$C_{26}H_{20}Cl_2N_6O$, MW=503.38 Mass Spec m/z (M$^+$+1) 503.01.

(k) 4-(6-{3-[3-(4-Chloro-phenyl)-ureido]-phenyl}-imidazo[1,2-a]pyrazin-8-ylamino)-benzoic acid ethyl ester, MF=$C_{28}H_{23}ClN_6O_3$, MW=526.97 Mass Spec m/z (M$^+$+1) 527.05.

(l) Cyclopropylmethyl-[6-(4-phenoxy-phenyl)-imidazo[1,2-a]pyrazin-8-yl]-amine, MF=$C_{22}H_{20}N_4O$, MW=356.42 Mass Spec m/z (M$^+$+1) 357.19.

(m) (2-Methoxy-benzyl)-[6-(4-phenoxy-phenyl)-imidazo[1,2-a]pyrazin-8-yl]-amine, MF=$C_{26}H_{22}N_4O_2$, MW=422.48 Mass Spec m/z (M$^+$+1) 423.19.

(n) Benzo[1,3]dioxol-5-ylmethyl-[6-(4-phenoxy-phenyl)-imidazo[1,2-a]pyrazin-8-yl]-amine, MF=$C_{26}H_{20}N_4O_3$, MW=436.46 Mass Spec m/z (M$^+$+1) 437.18.

(o) [6-(4-Chloromethyl-phenyl)-imidazo[1,2-a]pyrazin-8-yl]-(2-methoxy-benzyl)-amine, MF=$C_{21}H_{19}ClN_4O$, MW=378.85 Mass Spec m/z (M$^+$+1) 379.13.

(p) 1-{4-[8-(2-Methoxy-benzylamino)-imidazo[1,2-a]pyrazin-6-yl]-phenyl}-3-phenyl-urea, MF=$C_{27}H_{24}N_6O_2$, MW=464.52 Mass Spec m/z (M$^+$+1) 465.07.

(q) (2-Methoxy-benzyl)-{6-[4-(4-methoxy-benzylamino)-phenyl]-imidazo[1,2-a]pyrazin-8-yl}-amine, MF=$C_{28}H_{27}N_5O_2$, MW=465.55 Mass Spec m/z (M$^+$+1) 466.10.

(r) (2-Methoxy-benzyl)-{6-[3-(4-methoxy-benzylamino)-phenyl]-imidazo[1,2-a]pyrazin-8-yl}-amine, MF=$C_{28}H_{27}N_5O_2$, MW=465.55 Mass Spec m/z (M$^+$+1) 466.09.

(s) 1-{3-[8-(2-Methoxy-benzylamino)-imidazo[1,2-a]pyrazin-6-yl]-phenyl}-3-phenyl-urea, MF=$C_{27}H_{24}N_6O_2$, MW=464.52 Mass Spec m/z (M$^+$+1) 465.05.

(t) 1-(2-Chloro-phenyl)-3-{4-[8-(2-methoxy-benzylamino)-imidazo[1,2-a]pyrazin-6-yl]-phenyl}-urea, MF=$C_{27}H_{23}ClN_6O_2$, MW=498.96 Mass Spec m/z (M$^+$+1) 499.18.

(u) 1-{4-[8-(2-Methoxy-benzylamino)-imidazo[1,2-a]pyrazin-6-yl]-phenyl}-3-(2-methoxy-phenyl)-urea, MF=$C_{28}H_{26}N_6O_3$, MW=494.54 Mass Spec m/z (M$^+$+1) 495.22.

(v) 1-{4-[8-(2-Methoxy-benzylamino)-imidazo[1,2-a]pyrazin-6-yl]-phenyl}-3-(3-methoxy-phenyl)-urea, MF=$C_{28}H_{26}N_6O_3$, MW=494.54 Mass Spec m/z (M$^+$+1) 495.21.

(w) 4-{6-[4-(Piperidine-1-carbonyl)-phenyl]-imidazo[1,2-a]pyrazin-8-ylamino}-benzoic acid ethyl ester, MF=$C_{27}H_{27}N_5O_3$, MW=469.54 Mass Spec m/z (M$^+$+1) 470.08.

(x) 4-(6-{3-[3-(4-Chloro-phenyl)-ureido]-phenyl}-imidazo[1,2-a]pyrazin-8-ylamino)-benzoic acid ethyl ester, MF=$C_{28}H_{23}ClN_6O_3$, MW=526.97 Mass Spec m/z (M$^+$+1) 527.05.

(y) 4-(6-{3-[3-(2-Methylsulfanyl-phenyl)-ureido]-phenyl}-imidazo[1,2-a]pyrazin-8-ylamino)-benzoic acid ethyl ester, MF=$C_{29}H_{26}N_6O_3S$, MW=538.62 Mass Spec m/z (M$^+$+1) 539.18.

(z) {4-[8-(4-Chloro-phenylamino)-imidazo[1,2-a]pyrazin-6-yl]-phenyl}-piperidin-1-yl-methanone, MF=$C_{24}H_{22}ClN_5O$, MW=431.92 Mass Spec m/z (M$^+$+1) 432.03.

(aa) {4-[8-(2-Chloro-phenylamino)-imidazo[1,2-a]pyrazin-6-yl]-phenyl}-piperidin-1-yl-methanone, MF=$C_{24}H_{22}ClN_5O$, MW=431.92 Mass Spec m/z (M$^+$+1) 432.03.

(bb) 3-Methoxy-N-{4-[8-(2-methoxy-benzylamino)-imidazo[1,2-a]pyrazin-6-yl]-phenyl}-benzamide, MF=$C_{28}H_{25}N_5O_3$, MW=479.53 Mass Spec m/z (M$^+$+1) 479.99.

(cc) 1-(3-Chloro-4-fluoro-phenyl)-3-[3-(8-phenylamino-imidazo[1,2-a]pyrazin-6-yl)-phenyl]-urea, MF=$C_{25}H_{18}ClFN_6O$, MW=472.90 Mass Spec m/z (M$^+$+1) 473.01.

(dd) 1-(4-Chloro-phenyl)-3-[3-(8-phenylamino-imidazo[1,2-a]pyrazin-6-yl)-phenyl]-urea, MF=$C_{25}H_{19}ClN_6O$, MW=454.91 Mass Spec m/z (M$^+$+1) 455.04.

(ee) 1-[3-(8-Phenylamino-imidazo[1,2-a]pyrazin-6-yl)-phenyl]-3-(3-trifluoromethyl-phenyl)-urea, MF=$C_{26}H_{19}F_3N_6O$, MW=488.46 Mass Spec m/z (M$^+$+1) 489.01.

(ff) 1-(2-Chloro-5-trifluoromethyl-phenyl)-3-[3-(8-phenylamino-imidazo[1,2-a]pyrazin-6-yl)-phenyl]-urea, MF=$C_{26}H_{18}ClF_3N_6O$, MW=522.91 Mass Spec m/z (M$^+$+1) 523.11.

(gg) 1-(4-Chloro-phenyl)-3-{3-[8-(4-chloro-phenylamino)-imidazo[1,2-a]pyrazin-6-yl]-phenyl}-urea, MF=$C_{25}H_{18}Cl_2N_6O$, MW=489.36 Mass Spec m/z (M$^+$+1) 489.20.

(hh) 1-{3-[8-(4-Chloro-phenylamino)-imidazo[1,2-a]pyrazin-6-yl]-phenyl}-3-(3-trifluoromethyl-phenyl)-urea, MF=$C_{26}H_{18}ClF_3N_6O$, MW=522.91 Mass Spec m/z (M$^+$+1) 523.13.

(ii) 1-(3-Chloro-4-fluoro-phenyl)-3-{3-[8-(3-chloro-phenylamino)-imidazo[1,2-a]pyrazin-6-yl]-phenyl}-urea, MF=$C_{25}H_{17}Cl_2FN_6O$, MW=507.35 Mass Spec m/z (M$^+$+1) 507.13.

(jj) 1-(4-Chloro-phenyl)-3-{3-[8-(3-chloro-phenylamino)-imidazo[1,2-a]pyrazin-6-yl]-phenyl}-urea, MF=$C_{25}H_{18}Cl_2N_6O$, MW=489.36 Mass Spec m/z (M$^+$+1) 489.13.

(kk) 1-{3-[8-(3-Chloro-phenylamino)-imidazo[1,2-a]pyrazin-6-yl]-phenyl}-3-(3-trifluoromethyl-phenyl)- urea, MF=C$_{26}$H$_{18}$ClF$_3$N$_6$O, MW=522.91 Mass Spec m/z (M$^+$+1) 523.12.

(ll) 1-(3-Chloro-4-fluoro-phenyl)-3-{3-[8-(2-chloro-phenylamino)-imidazo[1,2-a]pyrazin-6-yl]-phenyl}-urea, MF=C$_{25}$H$_{17}$Cl$_2$FN$_6$O, MW=507.35 Mass Spec m/z (M$^+$+1) 507.09.

EXAMPLE 4

A generalized description the standard AKT-1 Kinase Assay that may be used to evaluate the inventive compounds is as follows.

In a final reaction volume of 40 microliters (μl), active recombinant N-terminus his-tagged AKT-1/PKBα kinase expressed in Sf21 cells (UBI #14-276; 50–100 nanogram; 19–38 nanomolar; about 4.5–9 mU) was incubated in 25 mM Tris pH 7.6; 5 mM Beta-glycerophosphate; 2 mM DTT; 100 μM sodium vanadate; 10 mM MgCl$_2$ in 96-well Pierce Reaci-Bind™ streptavidin-coated high binding capacity coated white plate (Pierce #15502) coated with saturating amounts of biotinylated Crosstide peptide (UBI #12-385; biotin-KGSGSGRPRTSSFAEG; 50 picomoles; about 1.25 μM) and initiated with the addition of 2.5 μCi $^{32}$P-γATP (specific activity 3000 Cu/mmole; 10 mCi/ml; about 21 nM). Compounds were tested initially in duplicate wells for determination of initial IC$_{50}$ inhibition in half log serial dilutions starting at 100 μM with a final concentration of 2% DMSO. Following a 30 min incubation at 30° C., the reaction was stopped by aspiration and 4×100 μl washes with TBS plus 0.05% Tween-20 prior to addition of 100 μl scintillant and counting in Beckman TopCount instrument. Percent inhibition was calculated as [1-((AVE CPM $_{compound}$-AVE CPM $_{no\ peptide\ background}$)/(AVE CPM $_{no\ compound\ MAX}$-AVE CPM $_{no\ peptide\ background}$)))* 100]. Staurosporine, a general ATP competitive kinase inhibitor was used as a reference compound and showed an IC50 of approximately 60–100 nM for AKT-1 in the current assay format. Approximate S/N ratios are 8–12× with AVE CPM of Maximum about 15 k and no peptide background about 1.5 K. Improved S/N ratios can be obtained using higher amounts of either AKT-1 kinase or $^{32}$P-γATP. Cold ATP was not added in current format but has been added at up to 200 μM in the presence of 5 μCi $^{32}$P-γATP resulting in S/N ratios of approximately 5–10×.

EXAMPLE 5

A generalized description the standard assay to evaluate modulation of cell growth in soft agar (using cell lines HCT-15 (colon cancer), MiaPaca2 (pancreatic cancer), MCF-7 (breast cancer) and a NIH3T3 clone stably over-expressing transfected myrAkt-1 human gene, for example) is as follows.

Preparation of the agar base layer: A quantity of 500 ml of 2×DMEM (phenol red free, Sigma Cat #D2902) is prepared, and sterile filtered. To that solution is added 10 ml of sodium pyruvate (Gibco, Cat #11360-070), 10 ml of penicillin/streptomycin (Gibco, Cat#15140-122), 10 ml of Glutamax (Gibco, cat# 33050-061) and 100 ml of heat-inactivated FBS (Gemini) to make 2×DMEM complete media stock. Two stock concentrations of Sea Plaque low melt agar (Biowhittaker, Cat #431097), 1%, and 0.6%, are prepared with ultra pure milliQ water, and sterilized by autoclaving. To prepare the agar base layer for a 12-well plate (Falcon #353042), 6 ml of the 2×DMEM stock is mixed with 6 ml of 1% agar stock, both at 37° C., and 1 ml of the resulting mixture is added to each well of the 12 well plate, 3 hrs prior to setup of top layer.

Top layer with cells and compound for evaluation: Cells at 60–80% confluency (log growth) in T75 are trypsinized with 1 ml of 1× trypsin solution (Gibco), neutralized with 10 ml of 1×DMEM 10% FBS and viable cells counted using a hemocytometer via trypan blue exclusion. A working stock of 2.5×10$^4$ cells/ml is prepared in 1×DMEM 10% FBS. A 15 ml centrifuge tube is prepared for each concentration of compound tested in duplicate wells of a 12 well plate. The following are added in order: 1 ml of 2×DMEM stock at 37° C.; compound at 2× final desired concentration (using 4 microliter volume from a 1000× concentrated dilution series in 100% DMSO); followed by 2,500 cells (using 100 microliters of 1×10$^4$ cell/ml working stock), and finally 1 ml of 0.6% agar stock at 37° C. Following careful mixing, 1 ml each is added to duplicate wells of the 12-well plate. The plate is then placed in a 37° C., 5% CO$_2$, humidified incubator for 10 to 14 days and read. Rapid diffusion of CPD throughout top and bottom agar layer results in final drug concentration of 1×.

Counting Colonies: After 10 days of incubation, the plates are removed from the incubator for photography and colony counting. Each well is scanned using an eyepiece with a micrometer guide and 5× phase optics. Colonies 50 micrometer or greater in diameter are scored as positive. Duplicate wells are averaged and percent inhibition calculated using number of colonies in no compound control wells as 100%.

All compounds described in Examples 1–3 were tested in accordance with the protocols of Examples 4–5 and determined to exhibit an IC$_{50}$ value less than or equal to 25 micromolar.

All cited references are incorporated herein in their entirety. While preferred embodiments have been shown and described, various modifications and substitutions may be made thereto without departing from the spirit and scope of the invention. Accordingly, it is to be understood that the present invention has been described by way of illustration and not limitations.

What is claimed is:

1. At least one chemical entity chosen from compounds of Formula 10

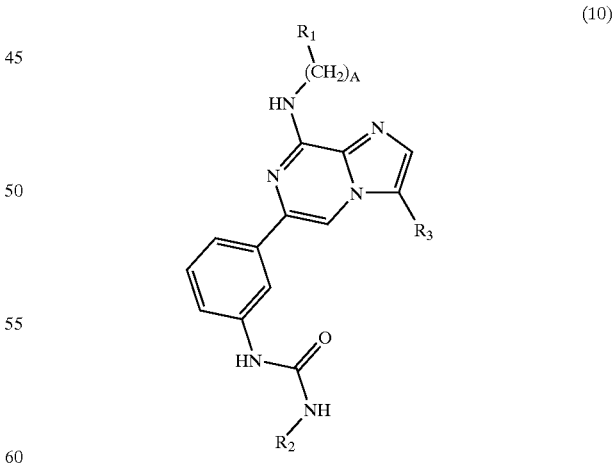

(10)

and pharmaceutically acceptable salts, hydrates, and diastereomers, wherein

R$_1$ is chosen from phenyl and substituted phenyl, wherein said substituted phenyl is chosen from mono-, di- and trisubstituted phenyls, and wherein substituents are independently chosen from hydroxy, nitro, cyano, amino, sulfonamide, halo, $C_1$–$C_6$ alkyl, $C_1$–$C_6$ perfluoroalkyl, $C_1$–$C_6$ perfluoroalkoxy, $C_1$–$C_6$ alkoxy, mono($C_1$–$C_6$ alkyl)amino, di($C_1$–$C_6$ alkyl)amino, mono($C_1$–$C_6$ alkyl)amino($C_1$–$C_6$ alkyl), and di($C_1$–$C_6$ alkyl)amino($C_1$–$C_6$ alkyl); and $R_2$ is chosen from phenyl and substituted phenyl, wherein said substituted phenyl is chosen from mono-, di- and trisubstituted phenyls and wherein substitutents are chosen from hydroxy, nitro, cyano, amino, halo, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono($C_1$–$C_6$ alkyl)amino, di($C_1$–$C_6$ alkyl)amino, and amino($C_1$–$C_6$ alkyl);

$R_3$ is chosen from hydrogen; and straight and branched chain $C_1$–$C_7$ alkyls, in which the branched alkyl chains may form a 3–7 member ring chosen from heteroalkyl rings and alkyl rings; and A is chosen from 0 and 1.

2. At least one chemical entity chosen from compounds of Formula 8

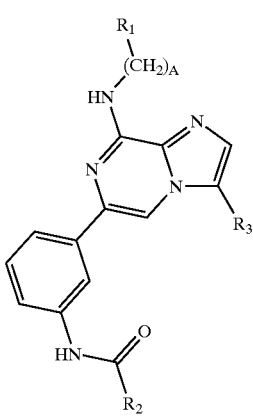

(8)

and pharmaceutically acceptable salts, hydrates, and diastereomers, wherein $R_1$ is chosen from phenyl and substituted phenyl, wherein said substituted phenyl is chosen from mono-, di- and trisubstituted phenyls and wherein substituents are independently chosen from hydroxy, nitro, cyano, amino, sulfonamide, halo, $C_1$–$C_6$ alkyl, $C_1$–$C_6$ perfluoroalkyl, $C_1$–$C_6$ perfluoroalkoxy, $C_1$–$C_6$ alkoxy, mono($C_1$–$C_6$ alkyl)amino, di($C_1$–$C_6$ alkyl)amino, mono($C_1$–$C_6$ alkyl)amino($C_1$–$C_6$ alkyl), and di($C_1$–$C_6$ alkyl)amino($C_1$–$C_6$ alkyl); and $R_2$ is chosen from phenyl and substituted phenyl, wherein said substituted phenyl is chosen from mono-, di- and trisubstituted phenyls, and wherein substituents are independently chosen from hydroxy, nitro, cyano, amino, halo, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono($C_1$–$C_6$ alkyl)amino, di($C_1$–$C_6$ alkyl)amino, and amino($C_1$–$C_6$ alkyl);

$R_3$ is chosen from hydrogen; and straight and branched chain $C_1$–$C_7$ alkyls, in which the branched alkyl chains may form a 3–7 member ring chosen from heteroalkyl rings and alkyl rings; and A is chosen from 0 and 1.

3. At least one chemical entity chosen from compounds of Formula 9:

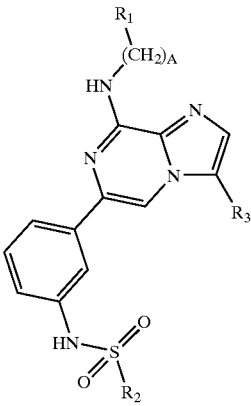

(9)

and pharmaceutically acceptable salts, hydrates, and diastereomers, wherein $R_1$ is chosen from phenyl and substituted phenyl, wherein said substituted phenyl is chosen from mono-, di- and trisubstituted phenyls and wherein substituents are independently chosen from hydroxy, nitro, cyano, amino, sulfonamide, halo, $C_1$–$C_6$ alkyl, $C_1$–$C_6$ perfluoroalkyl, $C_1$–$C_6$ perfluoroalkoxy, $C_1$–$C_6$ alkoxy, mono($C_1$–$C_6$ alkyl)amino, di($C_1$–$C_6$ alkyl)amino, mono($C_1$–$C_6$ alkyl)amino($C_1$–$C_6$ alkyl), and di($C_1$–$C_6$ alkyl)amino($C_1$–$C_6$ alkyl); and $R_2$ is chosen from phenyl and substituted phenyl, wherein said substituted phenyl is chosen from mono-, di- and trisubstituted phenyls and wherein substituents are independently chosen from hydroxy, nitro, cyano, amino, halo, $C_1$–$C_6$ alkyl, $C_1$–$C_6$ perfluoroalkyl, $C_1$–$C_6$ perfluoroalkoxy, $C_1$–$C_6$ alkoxy, ($C_1$–$C_6$)-alkyl-oxy-($C_1$–$C_6$)alkoxy, mono($C_1$–$C_6$ alkyl)amino, di($C_1$–$C_6$ alkyl)amino, and amino($C_1$–$C_6$ alkyl);

$R_3$ is chosen from hydrogen; and straight and branched chain $C_1$–$C_7$ alkyls, in which the branched alkyl chains may form a 3–7 member ring chosen from heteroalkyl rings and alkyl rings; and A is chosen from 0 and 1.

4. At least one chemical entity chosen from compounds of Formula 2

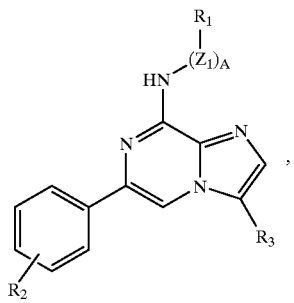

(2)

and pharmaceutically acceptable salts, hydrates, and diastereomers, wherein $R_1$ is chosen from
hydrogen;
cyclo-($C_3$–$C_6$ alkyl)-methyl;

straight and branched chain $C_1$–$C_7$ alkyls, in which the branched alkyl chains may form a 3–7 member ring chosen from heteroalkyl rings and alkyl rings;

sulfonamide;

$C_1$–$C_6$ alkoxy;

$(C_1$–$C_6)$-alkyl-oxy-$(C_1$–$C_6)$alkoxy;

mono$(C_1$–$C_6$ alkyl)amino;

di$(C_1$–$C_6$ alkyl)amino;

mono$(C_1$–$C_6$ alkyl)amino$(C_1$–$C_6$ alkyl);

di$(C_1$–$C_6$ alkyl)amino$(C_1$–$C_6$ alkyl);

phenyl;

heteroaryl;

substituted phenyl, wherein said substituted phenyl is chosen from mono-, di-, and trisubstituted phenyls and wherein substituents are independently chosen from hydroxy, nitro, cyano, amino, sulfonamide, halo, $C_1$–$C_6$ alkyl, $C_1$–$C_6$ perfluoroalkyl, $C_1$–$C_6$ perfluoroalkoxy, $C_1$–$C_6$ alkoxy, mono$(C_1$–$C_6$ alkyl) amino; di$(C_1$–$C_6$ alkyl)amino, mono$(C_1$–$C_6$ alkyl)amino$(C_1$–$C_6$ alkyl); and di$(C_1$–$C_6$ alkyl)amino$(C_1$–$C_6$ alkyl); and substituted heteroaryl, wherein said substituted heteroaryl is chosen from mono-, di- and trisubstituted heteroaryls wherein substituents are independently chosen from hydroxy, nitro, cyano, amino, sulfonamide, halo, $C_1$–$C_6$ alkyl, $C_1$–$C_6$ perfluoroalkyl, $C_1$–$C_6$ perfluoroalkoxy, $C_1$–$C_6$ alkoxy, mono$(C_1$–$C_6$ alkyl) amino, di$(C_1$–$C_6$ alkyl)amino, mono$(C_1$–$C_6$ alkyl)amino$(C_1$–$C_6$ alkyl); and di$(C_1$–$C_6$ alkyl)amino$(C_1$–$C_6$ alkyl);

$R_2$ is chosen from straight and branched chain $C_1$–$C_7$ alkyls, in which the branched alkyl chains may form a 3–7 member ring chosen from heteroalkyl rings and alkyl rings;

cyclo-$(C_3$–$C_6$ alkyl)-methyl;

$C_1$–$C_6$ alkoxy except when A is 0 and $R_1$ is chosen from straight and branched chain $C_1$–$C_7$ alkyls (but not cycloalkyl), phenyl, and substituted phenyl wherein substituents are independently chosen from hydroxy, nitro, cyano, amino, $C_1$–$C_6$ alkoxy, and halo; and when A is 1 and $Z_1$ is —$C(R_4)(R_5)$— wherein m is chosen from 1, 2, and 3 and $R_1$ is chosen from straight and branched chain $C_1$–$C_7$ alkyls (but not cycloalkyl), phenyl, and substituted phenyl wherein substituents are independently chosen from hydroxy, nitro, cyano, amino, $C_1$–$C_6$ alkoxy, and halo;

$(C_1$–$C_6)$-alkyl-oxy-$(C_1$–$C_6)$alkoxy;

phenyl;

substituted phenyl, wherein said substituted phenyl is chosen from mono-, di-, and trisubstituted phenyls and wherein substituents are independently chosen from hydroxy, nitro, cyano, amino, sulfonamide, halo, $C_1$–$C_6$ alkyl, $C_1$–$C_6$ perfluoroalkyl, $C_1$–$C_6$ perfluoroalkoxy, $C_1$–$C_6$ alkoxy, mono$(C_1$–$C_6$ alkyl) amino, di$(C_1$–$C_6$ alkyl)amino, mono$(C_1$–$C_6$ alkyl)amino$(C_1$–$C_6$ alkyl), and di$(C_1$–$C_6$ alkyl)amino$(C_1$–$C_6$ alkyl);

heteroaryl, and substituted heteroaryl, wherein said heteroaryl group is chosen from mono-, di- and trisubstituted heteroaryls and wherein substituents are independently chosen from hydroxy, nitro (except when A is 0 and $R_1$ is chosen from straight and branched chain $C_1$–$C_7$ alkyls (but not cycloalkyl), phenyl, and substituted phenyl wherein substituents are independently chosen from hydroxy, nitro, cyano, amino, $C_1$–$C_6$ alkoxy, and halo; and except when A is 1 and $Z_1$ is —$C(R_4)(R_6)$— wherein m is chosen from 1, 2, and 3, and $R_1$ is chosen from straight and branched chain $C_1$–$C_7$ alkyls (but not cycloalkyl), phenyl, substituted phenyl wherein substituents are independently chosen from hydroxy, nitro, cyano, amino, $C_1$–$C_6$ alkoxy, and halo), cyano, amino, halo, $C_1$–$C_6$ alkyl, $C_1$–$C_6$ perfluoroalkyl, $C_1$–$C_6$ perfluoroalkoxy, $C_1$–$C_6$ alkoxy, $(C_1$–$C_6)$-alkyl-oxy-$(C_1$–$C_6)$alkoxy, mono$(C_1$–$C_6$ alkyl)amino, di$(C_1$–$C_6$ alkyl)amino, and amino$(C_1$–$C_6$ alkyl);

phenyoxy phenyl;

substituted phenyoxy phenyl, where each phenyl is independently chosen from mono-, di- and trisubstituted phenyls wherein substituents are independently chosen from hydroxy, nitro, cyano, amino, halo, sulfonamide, $C_1$–$C_6$ alkyl, $C_1$–$C_6$ perfluoroalkyl, $C_1$–$C_6$ perfluoroalkoxy, $C_1$–$C_6$ alkoxy, $(C_1$–$C_6)$-alkyl-oxy-$(C_1$–$C_6)$alkoxy, mono$(C_1$–$C_6)$alkylamino), di$(C_1$–$C_6$ alkyl)amino, and amino$(C_1$–$C_6$ alkyl);

phenyl piperazine;

substituted phenyl piperazine, wherein the phenyl ring of said substituted phenyl piperazine is chosen from mono-, di-, and trisubstituted phenyls and wherein substitutents are chosen from hydroxy, nitro, cyano, amino, halo, sulfonamide, $C_1$–$C_6$ alkyl, $C_1$–$C_6$ perfluoroalkyl, $C_1$–$C_6$ perfluoroalkoxy, $C_1$–$C_6$ alkoxy, $(C_1$–$C_6)$-alkyl-oxy-$(C_1$–$C_6)$alkoxy, mono$(C_1$–$C_6$ alkyl) amino, di$(C_1$–$C_6$ alkyl)amino, mono$(C_1$–$C_6$ alkyl)amino$(C_1$–$C_6$ alkyl), and di$(C_1$–$C_6$ alkyl)amino$(C_1$–$C_6$ alkyl);

heteroaryl piperazine; and substituted heteroaryl piperazine where the heteroaryl ring of said substituted heteroaryl piperazine is chosen from mono-, di- and trisubstituted heteroaryls wherein substituents are independently chosen from hydroxy, nitro, cyano, amino, halo, sulfonamide, $C_1$–$C_6$ alkyl, $C_1$–$C_6$ perfluoroalkyl, $C_1$–$C_6$ perfluoroalkoxy, $C_1$–$C_6$ alkoxy, $(C_1$–$C_6)$-alkyl-oxy-$(C_1$–$C_6)$alkoxy mono $(C_1$–$C_6$ alkyl)amino, di$(C_1$–$C_6$ alkyl)amino, mono $(C_1$–$C_6$ alkyl)amino$(C_1$–$C_6$ alkyl), and di$(C_1$–$C_6$ alkyl)amino$(C_1$–$C_6$ alkyl);

$R_3$ is chosen from hydrogen; straight and branched chain $C_1$–$C_7$ alkyls, in which the branched alkyl chains can also form a 3–7 member ring chosen from heteroalkyl rings and alkyl rings;

A is chosen from 0 and 1; and
$Z_1$ is chosen from

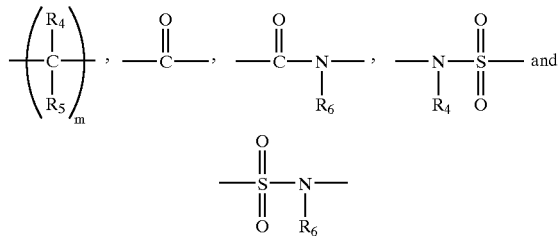

wherein
each occurrence of $R_4$ and $R_5$ is independently chosen from hydrogen, straight and branched chain $C_1-C_6$ alkyl, sulfonamide, and halo;
m is chosen from 1, 2, and 3; and
$R_6$ is chosen from
hydrogen;
straight and branched chain $C_1-C_6$ alkyl;
phenyl;
substituted phenyl, wherein said substituted phenyl is chosen from mono-, di- and trisubstituted phenyls and wherein substituents are independently chosen from hydroxy, nitro, cyano, amino, halo, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$alkoxy, mono$(C_1-C_6$ alkyl)amino, di$(C_1-C_6$ alkyl)amino, and amino$(C_1-C_6$ alkyl);
heteroaryl, and
substituted heteroaryl, which said substituted heteroaryl is chosen from mono-, di- and trisubstituted heteroaryls and wherein substituents are independently chosen from hydroxy, nitro, cyano, amino, halo, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$alkoxy, mono$(C_1-C_6$ alkyl)amino, di$(C_1-C_6$ alkyl)amino, and amino$(C_1-C_6$ alkyl).

5. At least one chemical entity chosen from compounds of Formula 3:

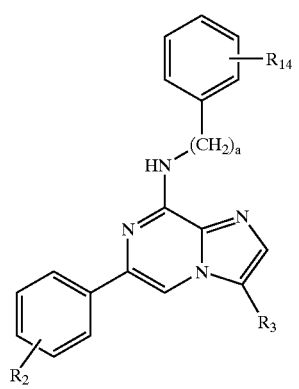

(3)

and pharmaceutically acceptable salts, hydrates, and diastereomers, wherein
a is chosen from 0, 1, 2 and 3;
$R_{14}$ is chosen from
hydrogen;
cyclo-$(C_3-C_6$ alkyl)-methyl;
straight and branched chain $C_1-C_6$ alkyl, in which the branched alkyl chains may form a 3–7 member ring chosen from heteroalkyl rings and alkyl rings;
sulfonamide;
$C_1-C_6$ alkoxy;
$(C_1-C_6)$-alkyl-oxy-$(C_1-C_6)$alkoxy;
mono$(C_1-C_6$ alkyl)amino;
di$(C_1-C_6$ alkyl)amino;
mono$(C_1-C_6$ alkyl)amino$(C_1-C_6$ alkyl);
di$(C_1-C_6$ alkyl)amino$(C_1-C_6$ alkyl);
phenyl;
substituted phenyl chosen from mono-, di-, and trisubstituted phenyls and wherein substituents are independently chosen from hydroxy, nitro, cyano, amino, sulfonamide, halo, $C_1-C_6$ alkyl, $C_1-C_6$ perfluoroalkyl, $C_1-C_6$ perfluoroalkoxy, $C_1-C_6$ alkoxy, mono$(C_1-C_6$ alkyl)amino, di$(C_1-C_6$ alkyl)amino, mono$(C_1-C_6$ alkyl)amino$(C_1-C_6$ alkyl); and di$(C_1-C_6$ alkyl)amino$(C_1-C_6$ alkyl);
heteroaryl; and
substituted heteroaryl wherein said substituted heteroaryl is chosen from mono-, di- and trisubstituted heteroaryls and wherein substituents are independently chosen from hydroxy, nitro, cyano, amino, sulfonamide, halo, $C_1-C_6$ alkyl, $C_1-C_6$ perfluoroalkyl, $C_1-C_6$ perfluoroalkoxy, $C_1-C_6$ alkoxy, mono$(C_1-C_6$ alkyl) amino, di$(C_1-C_6$ alkyl)amino, mono$(C_1-C_6$ alkyl) amino$(C_1-C_6$ alkyl), and di$(C_1-C_6$ alkyl)amino$(C_1-C_6$ alkyl);
$R_2$ is chosen from
straight and branched chain $C_1-C_6$ alkyls, in which the branched alkyl chains may form a 3–7 member ring chosen from heteroalkyl rings and alkyl rings;
cyclo-$(C_3-C_6$ alkyl)-methyl;
$C_1-C_6$ alkoxy;
phenyl;
substituted phenyl wherein said substituted phenyl is chosen from mono-, di-, and trisubstituted phenyls and wherein substituents are independently chosen from hydroxy, nitro, cyano, amino, halo, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$alkoxy, mono$(C_1-C_6$ alkyl) amino, di$(C_1-C_6$ alkyl)amino, and amino$(C_1-C_6$ alkyl);
heteroaryl; and
substituted heteroaryl, wherein said substituted heteroaryl is chosen from mono-, di- and trisubstituted heteroaryls and wherein substituents are independently chosen from hydroxy, nitro, cyano, amino, halo, $C_1-C_6$ alkyl, $C_1-C_6$ perfluoroalkyl, $C_1-C_6$ perfluoroalkoxy, $C_1-C_6$ alkoxy, $(C_1-C_6)$-alkyl-oxy-$(C_1-C_6)$alkoxy, mono $(C_1-C_6$ alkyl)amino, di$(C_1-C_6$ alkyl)amino, and amino $(C_1-C_6$ alkyl);
phenyoxy phenyl;
substituted phenoxy phenyl, in which each phenyl is independently chosen from mono-, di- and trisubstituted phenyls and wherein substituents are independently chosen from
hydroxy,
nitro,
cyano,
amino,
halo,
sulfonamide,
$C_1-C_6$ alkyl,
$C_1-C_6$ perfluoroalkyl, C₁–C₆ perfluoroalkoxy,
C₁–C₆ alkoxy,
(C₁–C₆)-alkyl-oxy-(C₁–C₆)alkoxy,
mono(C₁–C₆ alkyl)amino,
di(C₁–C₆ alkyl)amino, and
amino(C₁–C₆ alkyl);

phenyl piperazine, substituted phenyl piperazine, wherein said phenyl ring of said substituted phenyl piperazine is chosen from mono-, di-, and trisubstituted phenyls and wherein substituents are independently chosen from hydroxy, nitro, cyano, amino, halo, sulfonamide, C₁–C₆ alkyl, C₁–C₆ perfluoroalkyl, C₁–C₆ perfluoroalkoxy, C₁–C₆ alkoxy, (C₁–C₆)-alkyl-oxy-(C₁–C₆)alkoxy, mono (C₁–C₆ alkyl)amino, di(C₁–C₆ alkyl)amino, mono (C₁–C₆ alkyl)amino(C₁–C₆ alkyl), and di(C₁–C₆ alkyl) amino(C₁–C₆ alkyl);

heteroaryl piperazine; and substituted heteroaryl piperazine wherein said heteroaryl ring in said substituted heteroaryl piperazine is chosen from unsubstituted, mono-, di- and trisubstituted heteroaryls and wherein substituents are independently chosen from hydroxy, nitro, cyano, amino, halo, sulfonamide, C₁–C₆ alkyl, C₁–C₆ perfluoroalkyl, C₁–C₆ perfluoroalkoxy, C₁–C₆ alkoxy, (C₁–C₆)-alkyl-oxy-(C₁–C₆)alkoxy, mono(C₁–C₆ alkyl)amino, di(C₁–C₆ alkyl)amino, mono(C₁–C₆ alkyl)amino (C₁–C₆ alkyl), and di(C₁–C₆ alkyl)amino(C₁–C₆ alkyl); and R₃ is chosen from hydrogen; and straight and branched chain C₁–C₆ alkyl, in which the branched alkyl chains may form a 3–7 member ring chosen from heteroalkyl rings and alkyl rings.

6. At least one chemical entity chosen from:
1-(4-chloro-phenyl)-3-[3-(8-methylamino-imidazo[1,2-a]pyrazin-6-yl)-phenyl]-urea;
1-(4-chloro-phenyl)-3-{3-[8-(pyridin-3-ylamino)-imidazo[1,2-a]pyrazin-6-yl]-phenyl}-urea;
4-(6-{3-[3-(4-chlorophenyl)-ureido]-phenyl}-imidazo[1,2-a]pyrazin-8-ylamino)-benzoic acid ethyl ester;
cyclopropylmethyl-[6-(4-phenoxyphenyl), imidazo[1,2-a]pyrazin-8yl]-amine;
(2-methoxybenzyl)-[6-(4-phenoxyphenyl)-imidazo[1,2-a]pyrazin-8-yl]-amine;
benzo[1,3]dioxol-5-ylmethyl-[6-(4-phenoxyphenyl)-imidazo[1,2-a]pyrazin-8-yl]-amine;
[6-(4-(chloromethyl)phenyl)-imidazo[1,2-a]pyrazin-8-yl]-(2-methoxy-benzyl)-amine;
(2-methoxy-benzyl)-{6-[4-(4-methoxybenzylamino)-phenyl]-imidazo[1,2-a]pyrazin-8-yl}-amine;
(2-methoxy-benzyl)-{6-[3-(4-methoxybenzylamino)-phenyl]-imidazo[1,2-a]pyrazin-8-yl}-amine;
4-{6-[4-(piperidine-1-carbonyl)-phenyl]-imidazo[1,2-a]pyrazin-8-ylamino}-benzoic acid ethyl ester;
4-(6-{3-[3-(4-chlorophenyl)-ureido]-phenyl}-imidazo[1,2-a]pyrazin-8-ylamino)-benzoic acid ethyl ester;
4-(6-{3-[3-(2-methylsulfanyl-phenyl)-ureido]-phenyl}-imidazo[1,2-a]pyrazin-8-ylamino)-benzoic acid ethyl ester;
{4-[8-(4-chlorophenylamino)-imidazo[1,2-a]pyrazin-6-yl]-phenyl}-piperidin-1-yl-methanone;
{4-[8-(2-chlorophenylamino)-imidazo[1,2-a]pyrazin-6-yl]-phenyl}-piperidin-1-yl-methanone;
and pharmaceutically acceptable salts, hydrates, and diastereomers thereof.

7. At least one chemical entity of claim 1 chosen from 1-(4-chloro-phenyl)-3-[3-(8-phenylamino-imidazo[1,2-a]pyrazin-6-yl)-phenyl]-urea and pharmaceutically acceptable salts, hydrates, and diastereomers thereof.

8. At least one chemical entity of claim 1 chosen from 1-(4-chloro-phenyl)-3-{3-[8-(4-chlorophenylamino)-imidazo[1,2-a]pyrazin-6-yl]-phenyl}-urea and pharmaceutically acceptable salts, hydrates, and diastereomers thereof.

9. At least one chemical entity of claim 1 chosen from 1-(4-chloro-phenyl)-3-{3-[8-(3-chlorophenylamino)-imidazo[1,2-a]pyrazin-6-yl]-phenyl}-urea and pharmaceutically acceptable salts, hydrates, and diastereomers thereof.

10. At least one chemical entity of claim 1 chosen from 1-(4-chloro-phenyl)-3-{3-[8-(2-chlorophenylamino)-imidazo[1,2-a]pyrazin-6-yl]-phenyl}-urea and pharmaceutically acceptable salts, hydrates, and diastereomers thereof.

11. At least one chemical entity of claim 1 chosen from 1-{3-[8-(4-chlorobenzylamino)-imidazo[1,2-a]pyrazin-6-yl]-phenyl}-3-(4-chloro-phenyl)-urea and pharmaceutically acceptable salts, hydrates, and diastereomers thereof.

12. At least one chemical entity of claim 1 chosen from 1-{3-[8-(3-chlorobenzylamino)-imidazo[1,2-a]pyrazin-6-yl]-phenyl}-3-(4-chloro-phenyl)-urea and pharmaceutically acceptable salts, hydrates, and diastereomers thereof.

13. At least one chemical entity of claim 1 chosen from 1-{4-[8-(4-chlorobenzylamino)-imidazo[1,2-a]pyrazin-6-yl]-phenyl}-3-(4-chloro-phenyl)-urea and pharmaceutically acceptable salts, hydrates, and diastereomers thereof.

14. At least one chemical entity of claim 1 chosen from 1-{4-[8-(3-chlorobenzylamino)-imidazo[1,2-a]pyrazin-6-yl]-phenyl}-3-(4-chloro-phenyl)-urea and pharmaceutically acceptable salts, hydrates, and diastereomers thereof.

15. At least one chemical entity of claim 1 chosen from 1-{4-[8-(2-methoxybenzylamino)-imidazo[1,2-a]pyrazin-6-yl]-phenyl}-3-phenyl-urea and pharmaceutically acceptable salts, hydrates, and diastereomers thereof.

16. At least one chemical entity of claim 1 chosen from 1-{3-[8-(2-methoxybenzylamino)-imidazo[1,2-a]pyrazin-6-yl]-phenyl}-3-phenyl-urea and pharmaceutically acceptable salts, hydrates, and diastereomers thereof.

17. At least one chemical entity of claim 1 chosen from 1-(2-chloro-phenyl)-3-{4-[8-(2-methoxybenzylamino)-imidazo[1,2-a]pyrazin-6-yl]-phenyl}-urea and pharmaceutically acceptable salts, hydrates, and diastereomers thereof.

18. At least one chemical entity of claim 1 chosen from 1-{4-[8-(2-methoxybenzylamino)-imidazo[1,2-a]pyrazin-6-yl]-phenyl}-3-(2-methoxy-phenyl)-urea and pharmaceutically acceptable salts, hydrates, and diastereomers thereof.

19. At least one chemical entity of claim 1 chosen from 1-{4-[8-(2-ethoxybenzylamino)-imidazo[1,2-a]pyrazin-6-yl]-phenyl}-3-(3-methoxy-phenyl)-urea and pharmaceutically acceptable salts, hydrates, and diastereomers thereof.

20. At least one chemical entity of claim 2 chosen from 3-methoxy-N-{4-[8-(2-methoxybenzylamino)-imidazo[1,2-a]pyrazin-6-yl]-phenyl}-benzamide and pharmaceutically acceptable salts, hydrates, and diastereomers thereof.

21. At least one chemical entity of claim 1 chosen from 1-(3-chloro-4-fluorophenyl)-3-[3-(8-phenylamino-imidazo[1,2-a]pyrazin-6-yl)-phenyl]-urea and pharmaceutically acceptable salts, hydrates, and diastereomers thereof.

22. At least one chemical entity of claim 1 chosen from 1-(4-chlorophenyl)-3-[3-(8-phenylamino-imidazo[1,2-a]pyrazin-6-yl)-phenyl]-urea and pharmaceutically acceptable salts, hydrates, and diastereomers thereof.

23. At least one chemical entity of claim 1 chosen from 1-[3-(8-phenylamino-imidazo[1,2-a]pyrazin-6-yl)-phenyl]-3-(3-trifluoromethyl-phenyl)-urea and pharmaceutically acceptable salts, hydrates, and diastereomers thereof.

24. At least one chemical entity of claim 1 chosen from 1-(2-chloro-5-trifluoromethyl-phenyl)-3-[3-(8-phenylamino-imidazo[1,2-a]pyrazin-6-yl)-phenyl]-urea and pharmaceutically acceptable salts, hydrates, and diastereomers thereof.

25. At least one chemical entity of claim 1 chosen from 1-(4-chlorophenyl)-3-{3-[8-(4-chlorophenylamino)-imidazo[1,2-a]pyrazin-6-yl]-phenyl}-urea and pharmaceutically acceptable salts, hydrates, and diastereomers thereof.

26. At least one chemical entity of claim 1 chosen from 1-{3-[8-(4-chloro-phenylamino)-imidazo[1,2-a]pyrazin-6-yl]-phenyl}-3-(3-trifluoromethylphenyl)-urea and pharmaceutically acceptable salts, hydrates, and diastereomers thereof.

27. At least one chemical entity of claim 1 chosen from 1-(3-chloro-4-fluorophenyl)-3-{3-[8-(3-chlorophenylamino)-imidazo[1,2-a]pyrazin-6-yl]-phenyl}-urea and pharmaceutically acceptable salts, hydrates, and diastereomers thereof.

28. At least one chemical entity of claim 1 chosen from 1-(4-chlorophenyl)-3-{3-[8-(3-chlorophenylamino)-imidazo[1,2-a]pyrazin-6-yl]-phenyl}-urea and pharmaceutically acceptable salts, hydrates, and diastereomers thereof.

29. At least one chemical entity of claim 1 chosen from 1-{3-[8-(3-chlorophenylamino)-imidazo[1,2-a]pyrazin-6-yl]-phenyl}-3-(3-trifluoromethylphenyl)-urea and pharmaceutically acceptable salts, hydrates, and diastereomers thereof.

30. At least one chemical entity of claim 1 chosen from 1-(3-chloro-4-fluorophenyl)-3-{3-[8-(2-chlorophenylamino)-imidazo[1,2-a]pyrazin-6-yl]-phenyl}-urea and pharmaceutically acceptable salts, hydrates, and diastereomers thereof.

31. At least one chemical entity of claim 1 wherein in an in vitro assay of inhibition of AKT-1 kinase, the at least one chemical entity exhibits an $IC_{50}$ value less than or equal to 25 micromolar.

32. At least one chemical entity of claim 1 wherein in an in vitro assay of modulation of cell growth in soft agar, the at least one chemical entity exhibits an $IC_{50}$ value less than or equal to 25 micromolar.

33. At least one chemical entity of claim 1 wherein in an in vitro assay of modulation of cell growth in soft agar, wherein the cells are chosen from HCT-15, MiaPaca-2, MCF-7, OVCAR-4, and A549 cells, the at least one chemical entity exhibits an $IC_{50}$ value less than or equal to 25 micromolar.

34. A pharmaceutical composition comprising at least one chemical entity of claim 1; and at least one pharmaceutically acceptable carrier or excipient.

* * * * *